(12) United States Patent
Burrows et al.

(10) Patent No.: US 6,989,393 B2
(45) Date of Patent: Jan. 24, 2006

(54) CCR5 MODULATORS BENZIMIDAZOLES OR BENZOTRIAZOLES

(75) Inventors: Jeremy Burrows, Macclesfield (GB); John Cumming, Macclesfield (GB); Thomas Mcinally, Loughborough (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 10/220,915

(22) PCT Filed: Mar. 6, 2001

(86) PCT No.: PCT/SE01/00470

§ 371 (c)(1), (2), (4) Date: Sep. 6, 2002

(87) PCT Pub. No.: WO01/66525

PCT Pub. Date: Sep. 13, 2001

(65) Prior Publication Data

US 2003/0119869 A1 Jun. 26, 2003

(30) Foreign Application Priority Data

Mar. 10, 2000 (GB) ............................. 0005642

(51) Int. Cl.
A61K 31/445 (2006.01)
C07D 401/04 (2006.01)

(52) U.S. Cl. ...................... 514/322; 514/253; 514/300; 514/318; 544/336; 546/118; 546/193; 546/199

(58) Field of Classification Search ................. 514/253, 514/318, 300, 322; 544/336; 546/118, 193, 546/199

See application file for complete search history.

(56) References Cited

U.S. PATENT DOCUMENTS

| | | | |
|---|---|---|---|
| 3,318,900 A | | 5/1967 | Janssen |
| 4,126,689 A | | 11/1978 | Sanczuk et al. |
| 4,278,677 A | | 7/1981 | Nedelec et al. |
| 4,410,528 A | * | 10/1983 | Teranishi et al. ........... 514/243 |
| 5,521,197 A | | 5/1996 | Audia |
| 6,172,067 B1 | * | 1/2001 | Ito et al. ................. 514/252.13 |
| 6,248,755 B1 | * | 6/2001 | Chapman et al. ........... 514/320 |
| 6,407,121 B1 | * | 6/2002 | Nagamine et al. .......... 514/320 |
| 6,432,981 B1 | * | 8/2002 | Finke et al. ................ 514/322 |
| 2003/0176693 A1 | * | 9/2003 | Tsushima et al. ............. 544/60 |

FOREIGN PATENT DOCUMENTS

| | | |
|---|---|---|
| EP | 1 069 124 A1 | 1/2001 |
| EP | 1 122 257 A1 | 8/2001 |
| WO | WO 97/40035 | 10/1997 |
| WO | WO 99/04794 | 2/1999 |
| WO | WO 99/17773 A1 | 4/1999 |
| WO | WO 99/36421 | 7/1999 |
| WO | WO 00/08013 | 2/2000 |
| WO | WO 00/38680 A1 | 7/2000 |
| WO | WO 00/59502 A1 | 10/2000 |
| WO | WO 00/76514 A1 | 12/2000 |
| WO | WO 01/25200 A1 | 4/2001 |

OTHER PUBLICATIONS

CAS Listing, 77 answers.*
Vandenberk et al. "1–benzazolylalkylpiperidines . . . " CA 87:23274 (1977).*
Sato et al. "Psychotropic agents . . . " CA 89:208915 (1978).*
Teranishie et al. "Piperidines derivatives . . . " CA 95:132947 (1981).*
Vartanyan et al. "Synthesis and biological activeity . . . " CA 98:4503 (1983).*
Fukuda et al. "Preparation of benzotriazole . . . " CA 123:340149 91995).*
Cohen et al. "Cytokine function: a study in biologic diversity" CA 125:31527 (1996).*
Cowley et al. "Preparation of 1–(3–phenyloxypropyl_piperidine . . . " CA 138:39189 (2002).*
Ahmed et al. "Novel synthesis of 1–aryl–9–alkyl–2,3,3a,4, 9,9a–hexahydro . . . " CA 79:92106 (1973).*
Makoto Sato et al., "Psychotropic Agents. 3.$^1$4–(4–Substituted piperidinyl)–1–(4–flurophenyl)–1–butanones with Potent Neuroleptic Activity," Journal of Medicinal Chemistry, vol. 21, No. 11, pp. 1116–1120 (1978).
Ethan Will Taylor et al., "Molecular Determinants for Recognition of RU 24969 Analogs at Central 5–Hydroxytryptamine Recognition Sites: Use of a Bilinear Function and Substituent Volumes to Describe Steric Fit," Molecular Pharmacology vol. 32, pp. 42–53, (1988).
Nomoto et al., "Studies on Cardiotonic Agents. I. Synthesis if Some Quinazoline Derivatives", *Chem. Pharm. Bull.* 38(6):1591–1595 (1990).
Obase et al., "New Antihypertensive Agents. III. Synthesis and Antihypertensive Actvity of Some Arylalkyl Piperidines Carrying a Heterocycle at the 4–Position", *Chem. Pharm. Bull.* 31(9):3186–3197 (1983).
Obase et al., "Synthesis of (1–Substituted Piperidin–4–yl)–1H–benzimidazoles and (I–Substituted Piperidin–4–yl)–3,4–dihydroguinazolines as Possible Antihypertensive Agents", *J. Het. Chem.*20:565–573 (1983).

* cited by examiner

Primary Examiner—Celia Chang
(74) Attorney, Agent, or Firm—Fish & Richardson P.C.

(57) ABSTRACT

The invention concerns compounds of formula (I), wherein the variables are defined herein; processes for preparing them, compositions comprising them and their use in modulating CCR5 receptor activity.

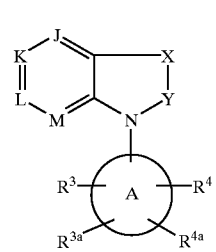

(I)

6 Claims, No Drawings

CCR5 MODULATORS BENZIMIDAZOLES OR BENZOTRIAZOLES

CROSS REFERENCE TO RELATED APPLICATIONS

The present application is a national phase application under 35 U.S.C. Section 371 filed from International Patent Application PCT/SE/01/0470, filed 6 Mar. 2001, which claims priority to United Kingdom patent application Serial No. 0005642.4, filed 10 Mar. 2000. The contents of these applications are incorporated herein by reference in their entirety.

The present invention relates to bicyclic heteroaryl derivatives having pharmaceutical activity, to processes for preparing such derivatives, to pharmaceutical compositions comprising such derivatives and to the use of such derivatives as active therapeutic agents.

Pharmaceutically active 1-(piperidin-4-yl)benzimidazole derivatives are disclosed in U.S. Pat. No. 3,318,900, WO97/40035, WO99/04794, WO99/36421, EP-A1-1069124 and J. Med. Chem. (1978) 21(11) 1116–1120.

Chemokines are chemotactic cytokines that are released by a wide variety of cells to attract macrophages, T cells, eosinophils, basophils and neutrophils to sites of inflammation and also play a role in the maturation of cells of the immune system. There are two classes of chemokine, C—X—C ($\alpha$) and C—C ($\beta$) depending on whether the first two cystines are separated by a single amino acid (C—X—C) or are adjacent (C—C). CCR5 is an example of a $\beta$-chemokine receptor.

The CCR5 receptor is expressed on T-lymphocytes, monocytes, macrophages, dendritic cells, microglia and other cell types. These detect and respond to several chemokines, principally "regulated on activation normal T-cell expressed and secreted" (RANTES), macrophage inflammatory proteins (MIP) MIP-1a and MIP-1b and monocyte chemoattractant protein-2 (MCP-2).

This results in the recruitment of cells of the immune system to sites of disease. In many diseases it is the cells expressing CCR5 which contribute, directly or indirectly, to tissue damage. Consequently, inhibiting the recruitment of these cells is beneficial in a wide range of diseases.

CCR5 is also a co-receptor for HIV-1 and other viruses, allowing these viruses to enter cells. Blocking the receptor with a CCR5 antagonist protects cells from viral infection.

The present invention provides a compound of formula (I):

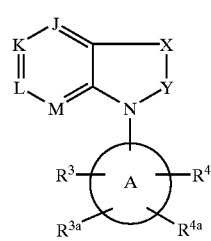

(I)

wherein
A is a 5, 6 or 7 membered ring comprising, respectively, 4, 5 or 6 carbons and one nitrogen which carries a substituent $R^1$. A being either saturated or including one endocyclic double bond;
X—Y is N=C($R^5$) or N=N;
J is N or $CR^{2a}$; K is N or $CR^{2b}$; L is N or $CR^{2c}$; M is N or $CR^{2d}$; provided that no more than 2 of J, K L and M are N;
$R^{2a}$, $R^{2b}$, $R^{2c}$ and $R^{2d}$ are, independently, hydrogen, halo, cyano, nitro, hydroxy, SH, S(O)$_p$$R^6$, $NR^7R^8$, $SO_2NR^9R^{10}$, $CONR^{11}R^{12}$, $NR^{13}SO_2R^{14}$, $NR^{15}COR^{16}$, $COR^{17}$, $CO_2R^{18}$, $NR^{19}CONR^{20}R^{21}$, $C_{1-6}$ alkyl, $C_{3-6}$ cycloalkyl, $C_{2-6}$ alkenyl, $C_{2-6}$ alkenyloxy, $C_{2-6}$ alkynyl, $C_{1-6}$ haloalkyl, $C_{1-6}$ alkoxy, $C_{1-6}$ haloalkoxy, $C_{1-6}$ alkoxy($C_{1-6}$)alkyl or heterocyclyl, or phenyl, phenyl($C_{1-4}$)alkyl, phenoxy, phenyl($C_{1-4}$)alkoxy, heteroaryl, heteroaryl($C_{1-4}$)alkyl, heteroaryloxy or heteroaryl($C_{1-4}$) alkoxy, wherein any of the foregoing phenyl and heteroaryl moieties are optionally substituted with halo, hydroxy, cyano, $C_{1-4}$ alkyl or $C_{1-4}$ alkoxy;
$R^1$ is $C_{1-10}$ alkyl, $C_{3-7}$ cycloalkyl, $C_{3-8}$ alkenyl or $C_{3-8}$ alkynyl, each optionally substituted with one or more of: halo, hydroxy, cyano, nitro, $C_{1-6}$ alkoxy (itself optionally substituted by heterocyclyl or $CONR^{62}R^{63}$), $C_{3-7}$ cycloalkyl, $NR^{22}R^{23}$, $C(O)R^{24}$, $NR^{25}SO_2R^{26}$, $NR^{27}C(O)R^{28}$, $SO_2NR^{29}R^{30}$, $CONR^{31}R^{32}$, $NR^{33}CONR^{34}R^{35}$, $S(O)_m$ $R^{64}$, heterocyclyl, heterocycly, aryl, aryloxy, heteroaryl, heteroaryloxy, 9H-fluorenyl (optionally substituted with halo, hydroxy, cyano, $C_{1-6}$ alkyl, $C_{1-6}$ alkoxy, $C_{2-6}$ alkenyl, phenyl or phenyl($C_{1-4}$)alkyl), 9H-xanthenyl (optionally substituted with halo, hydroxy, cyano, $C_{1-6}$ alkyl, $C_{1-6}$ alkoxy, $C_{2-6}$ alkenyl, phenyl or phenyl($C_{1-4}$)alkyl) or dibenzo(a,d)cycloheptatrienyl (optionally substituted with halo. hydroxy, cyano, $C_{1-6}$ alkyl, $C_{1-6}$ alkoxy, $C_{2-6}$ alkenyl, phenyl or phenyl($C_{1-4}$) alkyl);
$R^3$, $R^{3a}$, $R^4$ and $R^{4a}$ are, independently, hydrogen, $C_{1-6}$ alkyl (optionally substituted by hydroxy or alkoxy), $CO_2R^{36}$ or $CONR^{37}R^{38}$ (wherein $R^{36}$, $R^{37}$ and $R^{38}$ are, independently, hydrogen or $C_{1-6}$ alkyl);
$R^5$ is hydrogen, $C_{1-6}$ alkyl (optionally substituted with cyano, hydroxy, $C_{1-4}$ alkoxy, $C_{3-7}$ cycloalkyl, $COR^{58}$, $SO_2NR^{58}R^{59}$, $C(O)NR^{75}R^{76}$, $NR^{74}COR^{65}$, $NR^{73}SO_2R^{66}$, $NHC(O)NR^{67}R^{72}$, $NR^{68}R^{69}$, $SO_2R^{77}$, $C(O)R^{78}$, heterocyclyl, phenyl or heteroaryl), $C_{3-6}$ alkenyl, $C_{3-6}$ alkynyl, $C_{3-7}$ cycloalkyl, phenyl, heterocyclyl, heteroaryl, $OR^{79}$, $SR^{79}$, $CONR^{39}R^{40}$, $COR^{39}$, $NR^{39}R^{40}$, (wherein $R^{39}$ and $R^{40}$ are, independently, hydrogen, $C_{1-6}$ alkyl (optionally substituted with $C_{3-7}$ cycloalkyl, phenyl or heteroaryl), $C_{2-6}$ alkenyl, $C_{2-6}$ alkynyl, $C_{1-6}$ cycloalkyl, phenyl or heteroaryl; and $R^{79}$ is $C_{1-6}$ alkyl (optionally substituted with $C_{3-7}$ cycloalkyl, phenyl or heteroaryl), $C_{3-6}$ alkenyl, $C_{3-6}$ alkynyl, $C_{3-7}$ cycloalkyl, phenyl or heteroaryl), $NR^{70}SO_2R^{71}$ or $NR^{70}C(O)R^{71}$ (wherein $R^{70}$, $R^{73}$ and $R^{74}$ are, independently, hydrogen, $C_{1-4}$ alkyl, $C_{2-4}$ alkenyl, $C_{2-4}$ alkynyl or $C_{3-6}$ cycloalkyl; and $R^{71}$ is $C_{1-6}$ alkyl, $C_{3-7}$ cycloalkyl, aryl or heteroaryl);
$R^{64}$ is alkyl, cycloalkyl, aryl or heteroaryl;
$R^{13}$, $R^{15}$, $R^{19}$, $R^{25}$, $R^{27}$, $R^{33}$, are, independently, hydrogen, $C_{1-6}$ alkyl or phenyl;
$R^6$, $R^{14}$ and $R^{26}$ are, independently, alkyl (optionally substituted by halo, hydroxy, $C_{1-6}$ alkoxy, $C_{1-6}$haloalkoxy or phenyl), phenyl or heteroaryl;
$R^7$, $R^8$, $R^9$, $R^{10}$, $R^{11}$, $R^{12}$, $R^{16}$, $R^{17}$, $R^{18}$, $R^{20}$, $R^{21}$, $R^{22}$, $R^{23}$, $R^{24}$, $R^{28}$, $R^{29}$, $R^{30}$, $R^{31}$, $R^{32}$, $R^{34}$, $R^{35}$, $R^{58}$, $R^{59}$, $R^{67}$, $R^{68}$, $R^{69}$, $R^{72}$, $R^{75}$ and $R^{76}$ are, independently, hydrogen or alkyl (optionally substituted by halo, hydroxy, $C_{1-6}$ alkoxy, $C_{1-6}$ haloalkoxy, heterocyclyl, $CONR^{60}R^{61}$, or phenyl (itself optionally substituted by halo, hydroxy, cyano, $C_{1-4}$ alkyl or $C_{1-4}$ alkoxy)), phenyl or heteroaryl; unless specified otherwise, the foregoing aryl, phenyl and heteroaryl moieties are optionally substituted with halo, cyano, nitro, hydroxy, $S(O)_qR^{41}$, $NR^{42}R^{43}$, $SO_2NR^{44}R^{45}$, $CONR^{46}R^{47}$, $NR^{48}SO_2R^{49}$, $NR^{51}COR^{52}$, $COR^{53}$, $CO_2R^{54}$, $NR^{55}CONR^{56}R^{57}$, $C_{1-6}$alkyl, $C_{3-6}$ cycloalkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxy($C_{1-6}$)alkyl, phenyl, phenyl($C_{1-4}$)alkyl, phenoxy, phenylthio, phenyl($C_{1-4}$)alkoxy, heteroaryl, heteroaryl($C_{1-4}$)alkyl, heteroaryloxy or heteroaryl($C_{1-4}$)alkoxy; wherein any of the immediately foregoing phenyl and heteroaryl moieties are optionally substituted with halo, hydroxy, cyano, $C_{1-4}$ alkyl or $C_{1-4}$ alkoxy;

$R^{48}$, $R^{51}$ and $R^{55}$ are, independently, hydrogen, $C_{1-6}$ alkyl or phenyl;

$R^{41}$, $R^{49}$ $R^{66}$ are, independently, alkyl (optionally substituted by halo, hydroxy, $C_{1-6}$ alkoxy, $C_{1-6}$ haloalkoxy or phenyl (itself optionally substituted by halo, hydroxy, cyano, $C_{1-4}$ alkyl or $C_{1-4}$ alkoxy)), phenyl or heteroaryl; $R^{42}$, $R^{43}$, $R^{44}$, $R^{45}$, $R^{46}$, $R^{47}$, $R^{52}$, $R^{53}$, $R^{54}$, $R^{56}$, $R^{57}$, $R^{60}$, $R^{61}$, $R^{62}$, $R^{63}$ and $R^{65}$ are, independently, hydrogen or alkyl (optionally substituted by halo, hydroxy, $C_{1-6}$ alkoxy, $C_{1-6}$ haloalkoxy or phenyl (itself optionally substituted by halo, hydroxy, cyano, $C_{1-4}$ alkyl or $C_{1-4}$ alkoxy)), phenyl or heteroaryl;

the pairs of substituents: $R^7$ and $R^8$, $R^9$ and $R^{10}$, $R^{11}$ and $R^{12}$, $R^{20}$ and $R^{21}$, $R^{22}$ and $R^{23}$, $R^{29}$ and $R^{30}$, $R^{31}$ and $R^{32}$, $R^{34}$ and $R^{35}$, $R^{37}$ and $R^{38}$, $R^{39}$ and $R^{40}$, $R^{42}$ and $R^{43}$, $R^{44}$ and $R^{45}$, $R^{46}$ and $R^{47}$, $R^{56}$ and $R^{57}$, $R^{58}$ and $R^{59}$, $R^{75}$ and $R^{76}$, $R^{67}$ and $R^{72}$ and $R^{68}$ and $R^{69}$ may, independently, join to form a ring and such a ring may also comprise an oxygen. sulphur or nitrogen atom;

$R^{77}$ and $R^{78}$ are, independently, N-linked heterocyclyl;

where for any of the foregoing heterocyclic groups having a ring —N(H)— moiety, that —N(H)— moiety may be optionally substituted by $C_{1-4}$ alkyl (itself optionally substituted by hydroxy), $C(O)(C_{1-4}$ alkyl), $C(O)NH(C_{1-4}$ alkyl), $C(O)N(C_{1-4}$ alkyl)$_2$ or $SO_2(C_{1-4}$ alkyl);

m, p and q are, independently, 0, 1 or 2;

a ring nitrogen and/or sulphur atom is optionally oxidised to form an N-oxide and/or an S-oxide;

or a pharmaceutically acceptable salt thereof

Certain compounds of the present invention can exist in different isomeric forms (such as enantiomers, diastereomers or geometric isomers). The present invention covers all such isomers and mixtures thereof in all proportions.

Suitable salts include acid addition salts such as hydrochlorides, hydrobromides or acetates.

The compounds of the invention may exist as solvates (such as hydrates) and the present invention covers all such solvates.

Alkyl groups and moieties are straight or branched chain and are, for example, methyl, ethyl, n-propyl or iso-propyl. Unless specified otherwise, alkyl groups preferably contain from 1 to 6 carbon atoms, especially from 1 to 4 carbon atoms.

Alkoxyalkyl is, for example, methoxymethyl, ethoxymethyl, 2-methoxyeth-1-yl or 2-ethoxyeth-1-yl.

Alkenyl and alkynyl groups and moieties are, for example, vinyl, allyl or propargyl.

Cycloalkyl is, for example, cyclopropyl, cyclopentyl or cyclohexyl.

Acyl is, for example, carbonyl substituted by $C_{1-6}$ alkyl or optionally substituted phenyl.

Halogen includes fluorine, chlorine, bromine and iodine. Preferably halogen is chlorine or fluorine.

Heterocyclyl is a non-aromatic 5 or 6 membered ring comprising at least one heteroatom selected from the group comprising nitrogen, oxygen and sulphur. Heterocyclyl is, for example, piperidinyl, morpholinyl, pyrrolidinyl, piperazinyl or tetrahydrofuryl.

Heteroaryl is an aromatic 5 or 6 membered ring comprising at least one heteroatom selected from the group comprising nitrogen, oxygen and sulphur. Heteroaryl is, for example, pyrrolyl, imidazolyl, pyrazolyl, 1,2,3-triazolyl, 1,2,4-triazolyl, oxazolyl, isoxazolyl, thiazolyl, isothiazolyl, pyridinyl, pyrimidinyl, pyrazinyl, pyridazinyl, thienyl, furyl, quinolinyl, isoquinolinyl, indolyl, benzimidazolyl, benzo[b]furyl or benzo[b]thienyl.

Aryl is a carbocyclic aromatic ring system (for example phenyl or naphthyl).

Phenyl($C_{1-4}$ alkyl) is, for example, benzyl or 2-phenyleth-1-yl. Phenyl($C_{1-4}$ alkoxy) is, for example, benzyloxy. Heteroaryl($C_{1-4}$alkyl) is, for example, pyridylmethyl or pyrimidinylmethyl. Heteroaryl($C_{1-4}$ alkoxy) is, for example, pyridylmethoxy or pyrimidinylmethoxy.

Haloalkyl is, for example $CF_3$. Haloalkoxy is, for example, $OCF_3$.

When $R^{39}$ and $R^{40}$ join to form a ring the ring is, for example, a piperazinyl, piperidinyl, pyrrolidinyl or morpholinyl ring.

The ring A is, for example, pyrrolidinyl, piperidinyl (such as piperidin-4-yl), homopiperidinyl or 1,2,3,6-tetrahydropyridinyl. Preferably A is piperidinyl (such as piperidin-4-yl).

In one particular aspect the present invention provides a compound of formula (Ia):

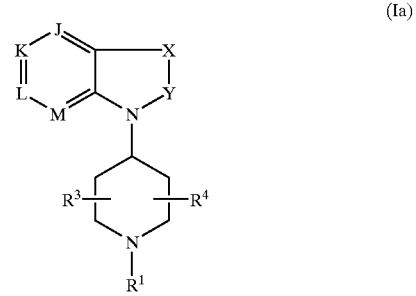

(Ia)

wherein J, K, L, M, X, Y, $R^1$, $R^3$ and $R^4$ are as defined above.

In a further aspect the present invention provides a compound of formula (Ib) or (Ic):

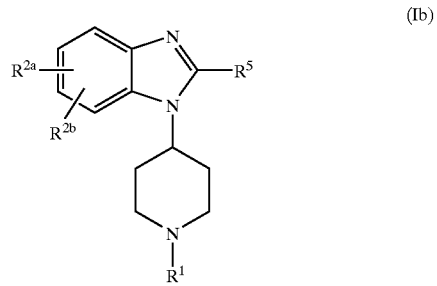

(Ib)

-continued

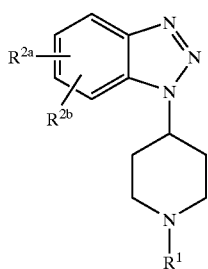
(Ic)

wherein $R^1$, $R^{2a}$, $R^{2b}$ and $R^5$ are as defined above.

In a further aspect the present invention provides a compound of formula (Ib') or (Ic'):

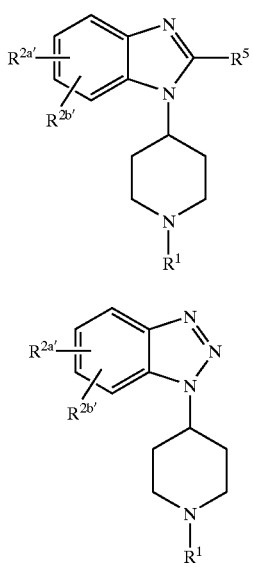

(Ib')

(Ic')

wherein $R^1$ and $R^5$ are as defined above; and the meanings of $R^{2a'}$ and $R^{2b'}$ are, independently, selected from the list recited above for $R^{2a}$ and $R^{2b}$.

In another aspect the invention provides a compound of formula (Id):

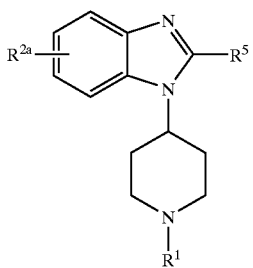

(Id)

wherein $R^1$ is $C_{1-10}$ alkyl optionally substituted with the substituents recited above; $R^{2a}$ is as defined above; and $R^5$ is hydrogen, $C_{1-6}$ alkyl (optionally substituted with $C_{3-7}$ cycloalkyl, $COR^{58}$, $SO_2NR^{58}R^{59}$, phenyl or heteroaryl), $C_{2-6}$ alkenyl, $C_{2-6}$ alkynyl, $C_{3-7}$ cycloalkyl, phenyl, heterocyclyl, heteroaryl, $OR^{79}$, $SR^{79}$, $CONR^{39}R^{40}$, $COR^{39}$ or $NR^{39}R^{40}$, (wherein $R^{58}$ and $R^{59}$ are, independently, hydrogen or $C_{1-4}$ alkyl; $R^{39}$ and $R^{40}$ are, independently, hydrogen, $C_{1-6}$ alkyl (optionally substituted with $C_{3-7}$ cycloalkyl, phenyl or heteroaryl), $C_{3-6}$ alkenyl, $C_{3-6}$ alkynyl, $C_{3-7}$ cycloalkyl, phenyl or heteroaryl; $R^{79}$ is $C_{1-6}$ alkyl (optionally substituted with $C_{3-7}$ cycloalkyl, phenyl or heteroaryl), $C_{3-6}$ alkenyl, $C_{3-6}$ alkynyl, $C_{3-7}$ cycloalkyl, phenyl or heteroaryl; wherein the phenyl and heteroaryl groups are optionally substituted as above.

In another aspect the invention provides a compound of formula (Id'):

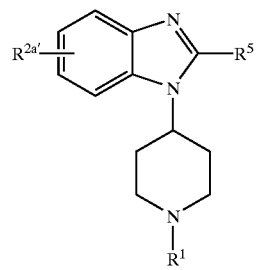

(Id')

wherein $R^1$ is $C_{1-10}$ alkyl optionally substituted with the substituents recited above; the meaning of $R^{2a'}$ is selected from the list recited above for $R^{2a}$; and $R^5$ is hydrogen, $C_{1-6}$ alkyl (optionally substituted with $C_{3-7}$ cycloalkyl, $COR^{58}$, $SO_2NR^{58}R^{59}$, phenyl or heteroaryl), $C_{2-6}$ alkenyl, $C_{2-6}$ alkynyl, $C_{3-7}$ cycloalkyl, phenyl, heterocyclyl, heteroaryl, $OR^{79}$, $SR^{79}$, $CONR^{39}R^{40}$, $COR^{39}$ or $NR^{39}R^{40}$, (wherein $R^{58}$ and $R^{59}$ are, independently, hydrogen or $C_{1-4}$ alkyl; $R^{39}$ and $R^{40}$ are, independently, hydrogen, $C_{1-6}$ alkyl (optionally substituted with $C_{3-7}$ cycloalkyl, phenyl or heteroaryl), $C_{3-6}$ alkenyl, $C_{3-6}$ alkynyl, $C_{3-7}$ cycloalkyl, phenyl or heteroaryl; $R^{79}$ is $C_{1-6}$ alkyl (optionally substituted with $C_{3-7}$ cycloalkyl, phenyl or heteroaryl), $C_{3-6}$ alkenyl, $C_{3-6}$ alkynyl, $C_{3-7}$ cycloalkyl, phenyl or heteroaryl; wherein the phenyl and heteroaryl groups are optionally substituted as above.

In a further aspect the present invention provides a compound of formula (Ie):

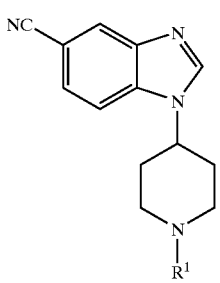

(Ie)

wherein $R^1$ is $C_{1-10}$ alkyl optionally substituted with the substituents recited above.

In yet another aspect the present invention provides a compound of formula (If):

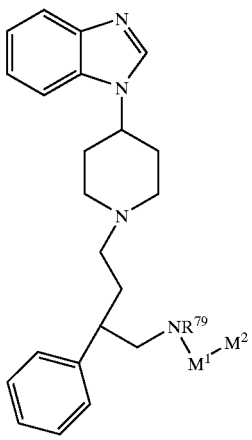

(If)

wherein $R^{79}$ is $C_{1-6}$ alkyl, $C_{3-6}$ cycloalkyl, phenyl or heteroaryl; $M^1$ is a bond, C(O), S(O)$_2$, S(O)$_2$NH or C(O)NH; and $M^2$ is $C_{1-6}$ alkyl, $C_{3-6}$ cycloalkyl, phenyl or heteroaryl; the phenyl and heteroaryl groups being optionally substituted as recited above.

In another aspect the present invention provides a compound of formula (I) or (Ia) wherein J is $CR^{2a}$, K is $CR^{2b}$; L is $CR^{2c}$; and M is N or $CR^{2d}$.

In another aspect the present invention provides a compound of formula (I) or (Ia) wherein X—Y is N=C($R^5$).

In a still further aspect the present invention provides a compound of formula (Ib) wherein $R^{2a}$ and $R^{2b}$ are, independently, hydrogen, halo, cyano, nitro, hydroxy, SH, S(O)$_p$R$^6$, NR$^7$R$^8$, SO$_2$NR$^9$R$^{10}$, CONR$^{11}$R$^{12}$, NR$^{13}$SO$_2$R$^{14}$, NR$^{15}$COR$^{16}$, COR$^{17}$, CO$_2$R$^{18}$, NR$^{19}$CONR$^{20}$R$^{21}$, $C_{1-6}$ alkyl, $C_{3-6}$ cycloalkyl, $C_{2-6}$ alkenyl, $C_{2-6}$ alkenyloxy, $C_{2-6}$ alkynyl, $C_{1-6}$ haloalkyl, $C_{1-6}$ alkoxy, $C_{1-6}$ haloalkoxy, $C_{1-6}$ alkoxy($C_{1-6}$)alkyl or heterocyclyl, or phenyl, phenyl($C_{1-4}$)alkyl, phenoxy, phenyl($C_{1-4}$)alkoxy, heteroaryl, heteroaryl($C_{1-4}$)alkyl, heteroaryloxy or heteroaryl($C_{1-4}$)alkoxy, wherein any of the foregoing phenyl and heteroaryl moieties are optionally substituted with halo, hydroxy, cyano, $C_{1-4}$ alkyl or $C_{1-4}$ alkoxy; $R^1$ is 2,4,6-trimethoxybenzyl, 2,4-dimethoxy-6-hydroxybenzyl, 3-(4-dimethylamino-phenyl) prop-2-enyl, (1-phenyl-2,5-dimethylpyrrol-3-yl)methyl, 2-phenylethyl, 3-phenylpropyl, 3-R/S-phenylbutyl, 3-cyano-3,3-diphenylpropyl, 3-cyano-3-phenylpropyl, 4-(N-methylbenzene-sulphonamido)-3-phenylbutyl, 4-(N-methylbenzamido)-3-phenylbutyl or 3,3-diphenylpropyl; $R^5$ is hydrogen, $C_{1-6}$ alkyl (optionally substituted with cyano, hydroxy, $C_{1-4}$ alkoxy, $C_{3-7}$ cycloalkyl, COR$^{58}$, SO$_2$NR$^{58}$R$^{59}$, C(O)NR$^{75}$R$^{76}$, NR$^{74}$COR$^{65}$, NR$^{73}$SO$_2$R$^{66}$, NHC(O)NR$^{67}$R$^{72}$, NR$^{68}$R$^{69}$, SO$_2$R$^{77}$, C(O)R$^{78}$, heterocyclyl, phenyl or heteroaryl), $C_{3-6}$ alkenyl, $C_{3-6}$ alkynyl, $C_{3-7}$ cycloalkyl, phenyl, heterocyclyl, heteroaryl, OR$^{79}$, SR$^{79}$, CONR$^{39}$R$^{40}$, COR$^{39}$, NR$^{39}$R$^{40}$, (wherein R$^{39}$ and R$^{40}$ are, independently, hydrogen, $C_{1-6}$ alkyl (optionally substituted with $C_{3-7}$ cycloalkyl, phenyl or heteroaryl), $C_{2-6}$ alkenyl, $C_{2-6}$ alkynyl, $C_{3-7}$ cycloalkyl, phenyl or heteroaryl; $R^{79}$ is $C_{1-6}$ alkyl (optionally substituted with $C_{3-7}$ cycloalkyl, phenyl or heteroaryl), $C_{3-6}$ alkenyl, $C_{3-6}$ alkynyl, $C_{3-7}$ cycloalkyl, phenyl or heteroaryl), NR$^{70}$SO$_2$R$^{71}$ or NR$^{70}$C(O)R$^{71}$ (wherein R$^{70}$, R$^{73}$ and R$^{74}$ are, independently, hydrogen, $C_{1-4}$ alkyl, $C_{2-4}$ alkenyl, $C_{2-4}$ alkynyl or $C_{3-6}$ cycloalkyl; and R$^{71}$ is $C_{1-6}$ alkyl, $C_{3-7}$ cycloalkyl, aryl or heteroaryl); R$^{13}$, R$^{15}$ and R$^{19}$ are, independently, hydrogen, $C_{1-6}$ alkyl or phenyl; R$^6$ and R$^{14}$ are, independently, alkyl (optionally substituted by halo, hydroxy, $C_{1-6}$ alkoxy, $C_{1-6}$ haloalkoxy or phenyl), phenyl or heteroaryl; R$^7$,R$^8$, R$^9$, R$^{10}$, R$^{11}$, R$^{12}$, R$^{16}$, R$^{17}$, R$^{18}$, R$^{20}$, R$^{21}$, R$^{58}$, R$^{59}$, R$^{67}$, R$^{68}$, R$^{69}$, R$^{72}$, R$^{75}$ and R$^{76}$ are, independently, hydrogen or alkyl (optionally substituted by halo, hydroxy, $C_{1-6}$ alkoxy, $C_{1-6}$ haloalkoxy, heterocyclyl, CONR$^{60}$R$^{61}$, or phenyl (itself optionally substituted by halo, hydroxy, cyano, $C_{1-4}$ alkyl or $C_{1-4}$ alkoxy)), phenyl or heteroaryl; unless specified otherwise, the foregoing aryl, phenyl and heteroaryl moieties are optionally substituted with halo, cyano, nitro, hydroxy, S(O)$_q$R$^{41}$, NR$^{42}$R$^{43}$, SO$_2$NR$^{44}$R$^{45}$, CONR$^{46}$R$^{47}$, NR$^{48}$SO$_2$R$^{49}$, NR$^{51}$COR$^{52}$, COR$^{53}$, CO$_2$R$^{54}$, NR$^{55}$CONR$^{56}$R$^{57}$, $C_{1-6}$ alkyl, $C_{3-6}$ cycloalkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkoxy($C_{1-6}$)alkyl, phenyl, phenyl($C_{1-4}$)alkyl, phenoxy, phenylthio, phenyl($C_{1-4}$)alkoxy, heteroaryl, heteroaryl($C_{1-4}$)alkyl, heteroaryloxy or heteroaryl($C_{1-4}$)alkoxy; wherein any of the immediately foregoing phenyl and heteroaryl moieties are optionally substituted with halo, hydroxy, cyano, $C_{1-4}$ alkyl or $C_{1-4}$ alkoxy; R$^{48}$, R$^{51}$ and R$^{55}$ are, independently, hydrogen, $C_{1-6}$ alkyl or phenyl; R$^{41}$, R$^{49}$R$^{66}$ are, independently, alkyl (optionally substituted by halo, hydroxy, $C_{1-6}$ alkoxy, $C_{1-6}$ haloalkoxy or phenyl (itself optionally substituted by halo, hydroxy, cyano, $C_{1-4}$ alkyl or $C_{1-4}$ alkoxy)), phenyl or heteroaryl; R$^{42}$, R$^{43}$, R$^{44}$, R$^{45}$, R$^{46}$, R$^{47}$, R$^{52}$, R$^{53}$, R$^{54}$, R$^{56}$, R$^{57}$, R$^{60}$, R$^{61}$ and R$^{65}$ are, independently, hydrogen or alkyl (optionally substituted by halo, hydroxy, $C_{1-6}$ alkoxy, $C_{1-6}$ haloalkoxy or phenyl (itself optionally substituted by halo, hydroxy, cyano, $C_{1-4}$ alkyl or $C_{1-4}$ alkoxy)), phenyl or heteroaryl; the pairs of substituents: R$^7$ and R$^8$, R$^9$ and R$^{10}$, R$^{11}$ and R$^{12}$, R$^{20}$ and R$^{21}$, R$^{37}$ and R$^{38}$, R$^{39}$ and R$^{40}$, R$^{42}$ and R$^{43}$, R$^{44}$ and R$^{45}$, R$^{46}$ and R$^{47}$, R$^{56}$ and R$^{57}$, R$^{58}$ and R$^{59}$, R$^{75}$ and R$^{76}$, R$^{67}$ and R$^{72}$ and R$^{68}$ and R$^{69}$ may, independently, join to form a ring and such a ring may also comprise an oxygen, sulphur or nitrogen atom; R$^{77}$ and R$^{78}$ are, independently, N-linked heterocyclyl; where for any of the foregoing heterocyclic groups having a ring —N(H)— moiety, that —N(H)— moiety may be optionally substituted by $C_{1-4}$ alkyl (itself optionally substituted by hydroxy), C(O)($C_{1-4}$ alkyl), C(O)NH($C_{1-4}$ alkyl), C(O)N($C_{1-4}$ alkyl)$_2$ or SO$_2$($C_{1-4}$ alkyl); m, p and q are, independently, 0, 1 or 2; a ring nitrogen and/or sulphur atom is optionally oxidised to form an N-oxide and/or an S-oxide; or a pharmaceutically acceptable salt thereof; provided that when $R^{2a}$ and $R^{2b}$ are both hydrogen and $R^5$ is hydrogen or methyl, then $R^1$ is not 2-phenylethyl.

In yet another aspect the present invention provides a compound of formula (Ib) wherein: $R^{2a}$, and $R^{2b}$ are, independently, hydrogen, halo, cyano, nitro, hydroxy, SH, S(O)$_p$R$^6$, NR$^7$R$^8$, SO$_2$NR$^9$R$^{10}$, CONR$^{11}$R$^{12}$, NR$^{13}$SO$_2$R$^{14}$, NR$^{15}$COR$^{16}$, COR$^{17}$CO$_{2R}$$^{18}$, NR$^{19}$CONR$^{20}$R$^{21}$, $C_{1-6}$ alkyl, $C_{3-6}$ cycloalkyl, $C_{2-6}$ alkenyl, $C_{2-6}$ alkenyloxy, $C_{2-6}$ alkynyl, $C_{1-6}$ haloalkyl, $C_{1-6}$ alkoxy, $C_{1-6}$ haloalkoxy, $C_{1-6}$ alkoxy ($C_{1-6}$)alkyl or heterocyclyl, or phenyl, phenyl($C_{1-4}$)alkyl, phenoxy, phenyl($C_{1-4}$)alkoxy, heteroaryl, heteroaryl($C_{1-4}$) alkyl, heteroaryloxy or heteroaryl($C_{1-4}$)alkoxy, wherein any of the foregoing phenyl and heteroaryl moieties are optionally substituted with halo, hydroxy, cyano, $C_{1-4}$ alkyl or $C_{1-4}$ alkoxy; R$^1$ is C$_{1-6}$ alkyl, C$_{3-7}$ cycloalkyl, C$_{3-8}$ alkenyl or C$_{3-8}$ alkynyl, each optionally substituted with one or more of: halo, hydroxy, cyano, nitro, C$_{1-6}$ alkoxy (itself optionally substituted by heterocyclyl or CONR$^{62}$R$^{63}$), C$_{3-7}$ cycloalkyl, NR$^{22}$R$^{23}$, C(O)R$^{24}$, NR$^{25}$SO$_2$R$^{26}$, NR$^{27}$C(O)R$^{28}$, SO$_2$NR$^{29}$R$^{30}$, CONR$^{31}$R$^{32}$, NR$^{33}$CONR$^{34}$R$^{35}$, S(O)$_m$R$^{64}$, heterocyclyl, heterocyclyloxy, aryl, aryloxy, heteroaryl or heteroaryloxy; R$^5$ is hydrogen: R$^{64}$ is alkyl, cycloalkyl, aryl or heteroaryl; R$^{13}$, R$^{15}$, R$^{19}$, R$^{25}$, R$^{27}$, R$^{33}$, are, independently, hydrogen, C$_{1-6}$ alkyl or phenyl; R$^6$, R$^{14}$ and R$^{26}$ are independently, alkyl (optionally substituted by halo, hydroxy, C$_{1-6}$ alkoxy, C$_{1-6}$ haloalkoxy or phenyl), phenyl or heteroaryl; R$^7$, R$^8$, R$^9$, R$^{10}$, R$^{11}$, R$^{12}$, R$^{16}$, R$^{17}$, R$^{18}$, R$^{20}$, R$^{21}$, R$^{22}$, R$^{23}$, R$^{24}$, R$^{28}$, R$^{29}$, R$^{30}$, R$^{31}$, R$^{32}$, R$^{34}$ and R$^{35}$ are, independently, hydrogen or alkyl (optionally substituted by halo, hydroxy, C$_{1-6}$ alkoxy, C$_{1-6}$ haloalkoxy, heterocyclyl, CONR$^{60}$R$^{61}$, or phenyl (itself optionally substituted by halo, hydroxy, cyano, C$_{1-4}$ alkyl or C$_{1-4}$ alkoxy)), phenyl or heteroaryl; unless specified otherwise, the foregoing aryl, phenyl and heteroaryl moieties are optionally substituted with halo, cyano, nitro, hydroxy, S(O)$_q$R$^{41}$, NR$^{42}$R$^{43}$, SO$_2$NR$^{44}$R$^{45}$, CONR$^{46}$R$^{47}$, NR$^{48}$SO$_2$R$^{49}$, NR$^{51}$COR$^{52}$, COR$^{53}$, CO$_2$R$^{54}$, NR$^{55}$CONR$^{56}$R$^{57}$, C$_{1-6}$ alkyl, C$_{3-6}$ cycloalkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{1-6}$ alkoxy(C$_{1-6}$)alkyl, phenyl, phenyl(C$_{1-4}$)alkyl, phenoxy, phenylthio, phenyl(C$_{1-4}$)alkoxy, heteroaryl, heteroaryl(C$_{1-4}$)alkyl, heteroaryloxy or heteroaryl(C$_{1-4}$)alkoxy; wherein any of the immediately foregoing phenyl and heteroaryl moieties are optionally substituted with halo, hydroxy, cyano, C$_{1-4}$ alkyl or C$_{1-4}$ alkoxy, R$^{48}$, R$^{51}$ and R$^{55}$ are, independently, hydrogen, C$_{1-6}$ alkyl or phenyl: R$^{41}$ and R$^{49}$ are, independently, alkyl (optionally substituted by halo, hydroxy, C$_{1-6}$ alkoxy, C$_{1-6}$ haloalkoxy or phenyl (itself optionally substituted by halo, hydroxy, cyano, C$_{1-4}$ alkyl or C$_{1-4}$ alkoxy)), phenyl or heteroaryl; R$^{42}$, R$^{43}$, R$^{44}$, R$^{45}$, R$^{46}$, R$^{47}$, R$^{52}$, R$^{53}$, R$^{54}$, R$^{56}$, R$^{57}$, R$^{60}$, R$^{61}$, R$^{62}$ and R$^{63}$ are, independently, hydrogen or alkyl (optionally substituted by halo, hydroxy, C$_{1-6}$ alkoxy, C$_{1-6}$ haloalkoxy or phenyl (itself optionally substituted by halo, hydroxy, cyano, C$_{1-4}$ alkyl or C$_{1-4}$ alkoxy)), phenyl or heteroaryl; the pairs of substituents: R$^7$ and R$^8$, R$^9$ and R$^{10}$, R$^{11}$ and R$^{12}$, R$^{20}$ and R$^{21}$, R$^{22}$ and R$^{23}$, R$^{29}$ and R$^{30}$, R$^{31}$ and R$^{32}$, R$^{34}$ and R$^{35}$, R$^{37}$ and R$^{38}$, R$^{42}$ and R$^{43}$, R$^{44}$ and R$^{45}$, R$^{46}$ and R$^{47}$ and R$^{56}$ and R$^{57}$ may independently, join to form a ring and such a ring may also comprise an oxygen, sulphur or nitrogen atom; where for any of the foregoing heterocyclic groups having a ring —N(H)— moiety, that —N(H)— moiety may be optionally substituted by C$_{1-4}$ alkyl (itself optionally substituted by hydroxy), C(O)(C$_{1-4}$ alkyl), C(O)NH(C$_{1-4}$ alkyl), C(O)N(C$_{1-4}$ alkyl)$_2$ or SO$_2$(C$_{1-4}$ alkyl); m, p and q are, independently, 0, 1 or 2; a ring nitrogen and/or sulphur atom is optionally oxidised to form an N-oxide and/or an S-oxide; or a pharmaceutically acceptable salt thereof; provided that when R$^{2a}$ and R$^{2b}$ are both hydrogen then R$^1$ is not methyl, benzyl, C$_{3-4}$ alkylene substituted once by tetrahydrophthalimide, 3-(4-fluorobenzoyl)propyl, (3,4-dihydro-2H-1-benzopyran-2-yl)methyl or a 3-(2-oxo-3,6-dihydro-4-methyl-6-(3,4-difluorophenyl)-2H-pyrimidin-1-ylcarbonylamino)propyl; and provided that when R$^{2a}$ is 5-fluoro and R$^{2b}$ is hydrogen then R$^1$ is not 2-(3-(4-fluorophenyl)-5-aminothiazol-2-yl)ethyl.

In a further aspect the present invention provides a compound as hereinbefore defined wherein R$^{2a}$ and R$^{2b}$ are, independently, hydrogen, halo, OH, CN, nitro, NH$_2$, NH(C$_{1-4}$ alkyl), N(C$_{1-4}$ alkyl)$_2$, NHC(O)(C$_{1-4}$ alkyl), N(C$_{1-4}$ alkyl)C(O)(C$_{1-4}$ alkyl), NHSO$_2$(C$_{1-4}$ alkyl), N(C$_{1-4}$ alkyl)SO$_2$(C$_{1-4}$ alkyl), SH, S(O)(C$_{1-4}$ alkyl), SO$_2$(C$_{1-4}$ alkyl), SO$_2$NH$_2$, SO$_2$NH(C$_{1-4}$ alkyl), SO$_2$N(C$_{1-4}$ alkyl)$_2$, CO$_2$H, CO$_2$(C$_{1-4}$ alkyl), C(O)NH$_2$, C(O)NH(C$_{1-4}$ alkyl), C(O)N(C$_{1-4}$ alkyl)$_2$, C$_{1-4}$ alkyl, C$_{1-4}$ alkoxy, C$_{1-4}$ haloalkyl, C$_{1-4}$ haloalkoxy, C$_{2-4}$ alkenyl, C$_{2-4}$ alkenyloxy, C$_{2-4}$ alkynyl, C(O)(C$_{1-4}$ alkyl), SCF$_3$, SO$_2$CF$_3$, phenyl, heterocyclyl or heteroaryl; the phenyl and heteroaryl groups being optionally substituted as recited above.

In another aspect the present invention provides a compound as hereinbefore described wherein R$^3$ and R$^4$ and, if present R$^{3a}$ and R$^{4a}$ are all hydrogen.

In a further aspect the invention provides a compound as hereinbefore described wherein R$^1$ is 2,6-dimethoxybenzyl, 2,4,6-trimethoxybenzyl, 2,4-dimethoxy-6-hydroxybenzyl, 3-(4-dimethylaminophenyl)prop-2-enyl, (1-phenyl-2,5-dimethylpyrrol-3-yl)methyl, 2-phenylethyl, 3-phenylpropyl, 3-R/S-phenylbutyl, 3-cyano-3,3-diphenylpropyl, 3-cyano-3-phenylpropyl, 4-(N-methylbenzene-sulphonamido)-3-phenylbutyl, 4-(N-methylbenzamido)-3-phenylbutyl or 3,3-diphenylpropyl.

In a still further aspect the invention provides a compound as hereinbefore described wherein R$^1$ is 3-R/S-phenylbutyl, 3-cyano-3,3-diphenylpropyl, 3-cyano-3-phenylpropyl, 4-(N-methylbenzenosulphonamido)-3-phenylbutyl, 4-(N-methylbenzamido)-3-phenylbutyl or, preferably, 3,3-diphenylpropyl.

In another aspect the present invention provides a compound of formula (Ig):

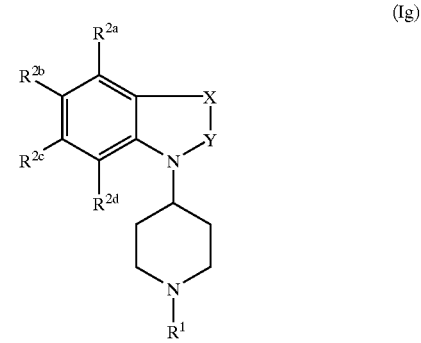

(Ig)

wherein X—Y is N=CH or N=N; R$^1$ is (CH$_2$)$_r$CHR'R"; R$^{2a}$ is hydrogen or halo (such as fluoro); R$^{2b}$ is hydrogen, halo (such as fluoro or chloro), CF$_3$, cyano or C$_{1-4}$ alkyl (such as methyl); R$^{2c}$ is hydrogen, halo (such as fluoro or chloro) or C$_{1-4}$ alkyl (such as methyl); R$^{2d}$ is hydrogen or halo (such as chloro); r is 2 or 3; R' is phenyl optionally substituted by halo (such as chloro); and, R" is C$_{1-4}$ alkyl (optionally mono-substituted with N(C$_{1-4}$ alkyl)SO$_2$phenyl) or phenyl.

In yet another aspect R$^5$ is hydrogen or C$_{1-4}$ alkyl (for example methyl). The group R$^5$ is particularly hydrogen.

In a further aspect the present invention provides a compound of formula (Ih):

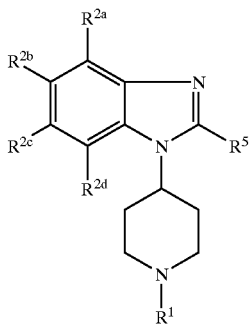

(Ih)

wherein
$R^1$ is $CR^{80}R^{81}CR^{82}R^{83}R^{84}$;
$R^{84}$ is $OR^{85}$, $NR^{86}R^{87}$ or $CR^{88}R^{89}R^{90}$;
$R^{80}$, $R^{81}$, $R^{82}$, $R^{83}$ and $R^{88}$ are, independently, hydrogen or $C_{1-4}$ alkyl (for example methyl);
$R^{85}$, $R^{87}$ and $R^{89}$ are phenyl or heteroaryl;
$R^{86}$ is hydrogen, $C_{1-4}$ alkyl, phenyl, heteroaryl, C(O)phenyl or C(O)heteroaryl;
$R^{90}$ is $C_{1-4}$ alkyl phenyl, heteroaryl, heterocyclyl, phenoxy, heteroaryloxy, NHC(O)($C_{1-6}$ alkyl), NHC(O)phenyl, NHC(O)heteroaryl, $C_{3-7}$ cycloalkyl, $CH_2C(O)(C_{1-6}$ alkyl), NHC(O)NH($C_{1-6}$ alkyl) or NHC(O)O($C_{1-6}$ alkyl);
$R^{2a}$, $R^{2b}$, $R^{2c}$ and $R^{2d}$ are, independently, hydrogen, halogen, cyano, $S(O)_2(C_{1-4}$ alkyl), $S(O)_2NH_2$, $S(O)_2NH(C_{1-4}$ alkyl) or $S(O)_2N(C_{1-4}$ alkyl)$_2$; and,
$R^5$ is hydrogen or $C_{1-4}$ alkyl (for example methyl), {$R^5$ is especially hydrogen};
wherein the foregoing phenyl and heteroaryl groups and moieties are optionally substituted by halogen (especially chlorine or fluorine) or $CF_3$.

In another aspect the present invention provides a compound as hereinbefore defined wherein $R^1$ is $CR^{80}R^{81}CR^{82}R^{83}R^{84}$; $R^{84}$ is $OR^{85}$, $NR^{86}R^{87}$ or $CR^{88}R^{89}R^{90}$; $R^{80}$, $R^{81}$, $R^{82}$, $R^{83}$ and $R^{88}$ are, independently, hydrogen or $C_{1-4}$ alkyl (for example methyl); $R^{85}$, $R^{87}$ and $R^{89}$ are phenyl or heteroaryl; $R^{86}$ is hydrogen, $C_{1-4}$ alkyl, phenyl, heteroaryl, C(O)phenyl or C(O)heteroaryl; and $R^{90}$ is $C_{1-4}$ alkyl, phenyl, heteroaryl, heterocyclyl, phenoxy, heteroaryloxy, NHC(O)($C_{1-6}$ alkyl), NHC(O)phenyl, NHC(O)heteroaryl, $C_{3-7}$ cycloalkyl, $CH_2C(O)(C_{1-6}$ alkyl), NHC(O)NH($C_{1-6}$ alkyl), NHC(O)O($C_{1-6}$ alkyl); wherein the foregoing phenyl and heteroaryl groups and moieties are optionally substituted by halogen (especially chlorine or fluorine) or $CF_3$.

In yet another aspect the present invention provides a compound of formula (Ih) wherein $R^{84}$ is $CR^{88}R^{89}R^{90}$.

In yet another aspect three of $R^{2a}$, $R^{2b}$, $R^{2c}$ and $R^{2d}$ are hydrogen and the other is $S(O)_2(C_{1-4}$ alkyl), $S(O)_2NH_2$, $S(O)_2NH(C_{1-4}$ alkyl) or $S(O)_2N(C_{1-4}$ alkyl)$_2$. In a further aspect $R^{2a}$, $R^{2c}$ and $R^{2d}$ are all hydrogen and $R^{2b}$ is $S(O)_2(C_{1-4}$ alkyl), $S(O)_2NH_2$, $S(O)_2NH(C_{1-4}$ alkyl) or $S(O)_2N(C_{1-4}$ alkyl)$_2$ {especially $R^{2b}$ is $S(O)_2(C_{1-4}$ alkyl), for example $S(O)_2CH_3$}.

In a further aspect the present invention provides a compound of formula (I) or (Ia) wherein J, L and M are as defined above; K is $CR^{2b}$; and $R^{2b}$ is $S(O)_2(C_{1-4}$ alkyl), $S(O)_2NH_2$, $S(O)_2NH(C_{1-4}$ alkyl) or $S(O)_2N(C_{1-4}$ alkyl)$_2$ {especially $R^{2b}$ is $S(O)_2(C_{1-4}$ alkyl), for example $S(O)_2CH_3$}.

In a still further aspect the present invention provides a compound of formula (Ij):

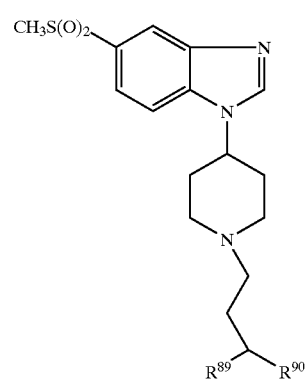

(Ij)

wherein $R^{89}$ and $R^{90}$ are as defined above.

When $R^1$ is 3-phenyl-butyl it is preferably in the form of the S-isomer.

Examples of compounds of the invention are provided in the Examples below and in the Tables hereunder.

TABLE I

Table I concern compounds of formula (Ij):

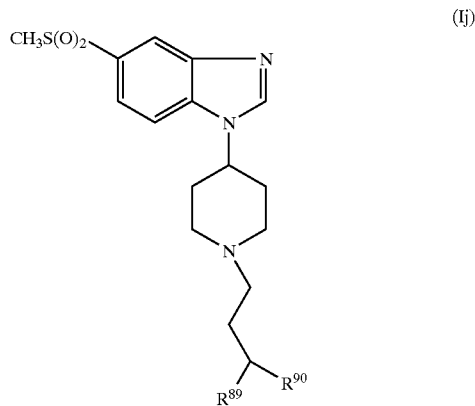

(Ij)

where $R^{89}$ and $R^{90}$ are as defined in the table below.

| Compound No. | $R^{89}$ | $R^{90}$ | Comment |
|---|---|---|---|
| 1 | Phenyl | Phenyl | |
| 2 | Phenyl | Methyl | |
| 3 | Phenyl | Methyl | S-isomer |
| 4 | Phenyl | Pyridin-2-yl | |
| 5 | Phenyl | Pyrimidin-2-yl | |
| 6 | 4-fluoro-phenyl | Pyridin-2-yl | |
| 7 | 4-$CF_3$-phenyl | Pyridin-2-yl | |
| 8 | 3-fluoro-phenyl | Pyridin-2-yl | |
| 9 | 3-fluoro-phenyl | Pyrazin-2-yl | |
| 10 | 3-fluoro-phenyl | NHC(O)phenyl | |
| 11 | 3-fluoro-phenyl | NHC(O)thien-3-yl | |
| 12 | 4-$CF_3$-phenyl | NHC(O)CH($CH_3$)$_2$ | |
| 13 | 4-$CF_3$-phenyl | NHC(O)NHCH($CH_3$)$_2$ | |
| 14 | Phenyl | 4-fluoro-phenyl | |
| 15 | 3-fluoro-phenyl | Thien-3-yl | |
| 16 | 3-fluoro-phenyl | Pyridin-3-yl | |
| 17 | Phenyl | Pyridin-2-yloxy | |
| 18 | Phenyl | 4-$CF_3$-phenyl | |
| 19 | Pyrimidin-4-yl | 3-chloro-phenyl | |
| 20 | 3-fluoro-phenyl | NHC(O)phenyl | |
| 21 | 4-$CF_3$-phenyl | NHC(O)thien-2-yl | |
| 22 | 4-$CF_3$-phenyl | $CH_2C(O)CH(CH_3)_2$ | |
| 23 | Phenyl | cyclobutyl | |
| 24 | Phenyl | phenoxy | |

TABLE I-continued

Table I concern compounds of formula (Ij):

(Ij)

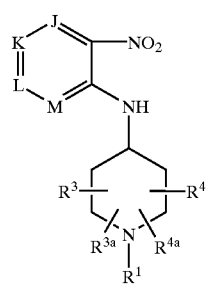

where $R^{89}$ and $R^{90}$ are as defined in the table below.

| Compound No. | $R^{89}$ | $R^{90}$ | Comment |
|---|---|---|---|
| 25 | 4-CF$_3$-phenyl | methyl | |
| 26 | 4-CF$_3$-phenyl | Methyl | S-isomer |
| 27 | 3-fluoro-phenyl | NHC(O)OCH(CH$_3$)$_2$ | |

The compounds of the invention can be prepared by adaptation of methods disclosed in the chemical art. For example compounds of formula (Ib), (Ic), (Ig), (Ih) and (Ik) can be prepared following the reaction sequences shown in Schemes 1 and 2 in which the reagents are as follows:
i. starting material can be prepared by adaptation of route described in EP309422; a fluoronitrobenzene or a chloronitrobenzene
ii. Raney nickel hydrogenation
iii. an alkylorthoformate
iv. hydrogenation (for example hydrogen in the presence of palladium of carbon catalyst)
v. reductive amination of aldehyde or alkylation with R"L (where L is a leaving group)
vi. Boc chloride or anhydride
vii. hydrogenation (for example hydrogen in the presence of palladium of carbon catalyst)
viii. reductive amination of aldehyde or alkylation with R"L (where L is a leaving group)
ix. trifluoroacetic acid
x. a fluoronitrobenzene or a chloronitrobenzene
xi. Raney nickel hydrogenation
xii. an alkylorthoformate Alternatively, compounds of formula (I), where A is piperidine, can be made by first reducing a compound of formula (II):

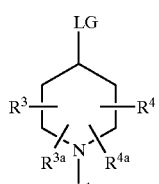

(II)

and then cyclising the product so formed. (For example, cyclising in the presence of NaNO$_2$ and dilute hydrochloric acid as 0–5° C. to produce a triazole ring; or cyclising in the presence of R$^5$CO$_2$H in refluxing toluene to produce an imidazole ring.)

A compound of formula (II) can be prepared by coupling a compound of formula (III):

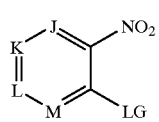

(III)

wherein LG is a leaving group (such as chlorine), with a compound of formula (IV):

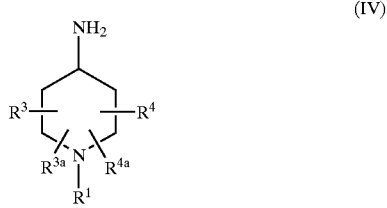

(IV)

in the presence of a base. Compounds of formula (III) can be made by nitration of the respective chloroheteroaryl or respective chloroheteroaryl N-oxide (followed by reduction to remove the N-oxide); or by chlorination of an oxo-nitro-heteroaryl (such as 3-nitropyridin-4-one).

Alternatively, compounds of formula (I), where A is piperidine, can be prepared by coupling a compound of formula (V):

(V)

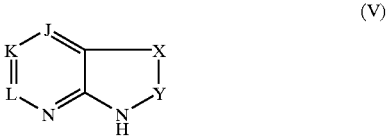

with a compound of formula (VI)

(VI)

wherein LG is a leaving group such as chlorine, tosyl or methylsulphonyl, in the presence of a base.

Compounds of formula (If) can be prepared by alkylation or reductive amination of a compound of formula (VII):

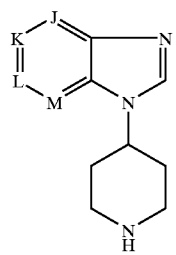

(VII)

for example alkylation with a compound of formula (IX):

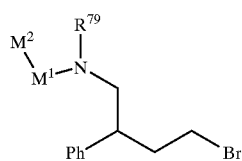

(IX)

Alternatively compounds of formula (I) can be prepared by preparing compounds of formula (VIII), for example as shown in Scheme 3, and then cyclising the compound of formula (VIII) as hereinbefore described.

Compounds of formula (I) wherein A is other than piperidine can be prepared by adaptation of literature methods or by adaptation of methodologies described above.

In another aspect the present invention provides processes for the preparation of compounds of formula (I), (Ia), (Ib), (Ic), (Id), (Ie), (If), (Ig), (Ih) and (Ij).

Many of the intermediates defined herein are novel and these are provided as a further feature of the invention.

By virtue of them being modulators (such as agonists, partial agonists, inverse agonists or antagonists) of the CCR5 receptor the compounds of the present invention are of value in the prevention or treatment of inflammatory and immunoregulatory disorders and diseases including asthma, allergic diseases and transplant rejection as well as autoimmune pathologies such as rheumatoid arthritis, atherosclerosis, psoriasis, systemic lupus erythematosus (SLE), ulcerative colitis, multiple sclerosis, glomerulonephritis, together with chronic obstructive pulmonary disease (COPD, including pulmonary fibrosis) and cerebral malaria. The compounds of the present invention are also of value in inhibiting the entry of viruses (such as human immunodeficiency virus (HIV)) into target calls and, therefore, are of value in the prevention of infection by viruses (such as HIV), the treatment of infection by viruses (such as HIV) and the prevention and/or treatment of acquired immune deficiency syndrome (AIDS).

According to a further feature of the invention there is provided a compound of the formula (I), (Ia), (Ib), (Ic), (Id), (Ie), (If), (Ig), (Ih) and (Ij), or a pharmaceutically acceptable salt thereof, for use in a method of treatment of the human or animal body by therapy According to a further feature of the present invention there is provided a method for modulating a CCR5 receptor in a warm blooded animal, such as man, in need of such treatment, which comprises administering to said animal an effective amount of a compound of the present invention, or a pharmaceutically acceptable salt thereof.

The invention also provides a compound of the formula (I), (Ia), (Ib), (Ic), (Id), (Ie), (If), (Ig), (Ih) and (Ij), or a pharmaceutically acceptable salt thereof for use as a medicament.

In another aspect the present invention provides the use of a compound of the formula (I), (Ia), (Ib), (Ic), (Id), (Ie), (If), (Ig), (Ih) and (Ij), or a pharmaceutically acceptable salt thereof, in the manufacture of a medicament for use in modulating a CCR5 receptor in a warm blooded animal, such as man.

The invention further provides the use of a compound of formula (I), (Ia), (Ib), (Ic), (Id), (Ie), (If), (Ig), (Ih) and (Ij), or a pharmaceutically acceptable salt thereof, in the manufacture of a medicament for use in the treatment of asthma, transplant rejection, rheumatoid arthritis, atherosclerosis, psoriasis, systemic lupus erythematosus, ulcerative colitis, multiple sclerosis, glomerulonephritis, chronic obstructive pulmonary disease, cerebral malaria, human immunodeficiency virus infection and acquired immune deficiency syndrome in a warm blooded animal, such as man.

The invention further provides the use of a compound of formula (I), (Ia), (Ib), (Ic), (Id), (Ie), (If), (Ig), (Ih) and (Ij), or a pharmaceutically acceptable salt thereof, in the manufacture of a medicament for use in the treatment of rheumatoid arthritis in a warm blooded animal, such as man.

The present invention further provides a method of treating a CCR5 mediated disease state in mammals which comprises administering to a mammal in need of such treatment an effective amount of a compound of formula (I), (Ia), (Ib), (Ic), (Id), (Ie), (If), (Ig), (Ih) and (Ij), or a pharmaceutically acceptable salt thereof.

The present invention further provides a method of treating rheumatoid arthritis in mammals which comprises administering to a mammal in need of such treatment an effective amount of a compound of formula (I), (Ia), (Ib), (Ic), (Id), (Ie), (If), (Ig), (Ih) and (Ij), or a pharmaceutically acceptable salt thereof.

In order to use a compound of the invention, or a pharmaceutically acceptable salt thereof, for the therapeutic treatment of mammals including humans, in particular modulating a CCR5 receptor, it is normally formulated in accordance with standard pharmaceutical practice as a pharmaceutical composition.

Therefore in another aspect the present invention provides a pharmaceutical composition which comprises a compound of the formula (I), (Ia), (Ib), (Ic), (Id), (Ie), (If), (Ig), (Ih) and (Ij), or a pharmaceutically acceptable salt thereof, and a pharmaceutically acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 10 mg and 1 g of the compound of this invention.

In another aspect a pharmaceutical composition of the invention is one suitable for intravenous, subcutaneous or intramuscular injection.

Each patient may receive, for example, an intravenous, subcutaneous or intramuscular dose of 0.1 mgkg$^{-1}$ to 100 mgkg$^{-1}$ of the compound, preferably in the range of 0.5 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I), (Ia), (Ib), (Ic), (Id), (Ie), (If), (Ig), (Ih) and (Ij), or a pharmaceutically-acceptable salt thereof (hereafter Compound X), for therapeutic or prophylactic use in humans:

(a)

| Tablet I | mg/tablet |
|---|---|
| Compound X | 100 |
| Lactose Ph.Eur. | 179 |
| Croscarmellose sodium | 12.0 |
| Polyvinylpyrrolidone | 6 |
| Magnesium stearate | 3.0 |

(b)

| Tablet II | mg/tablet |
|---|---|
| Compound X | 50 |
| Lactose Ph.Eur. | 229 |
| Croscarmellose sodium | 12.0 |
| Polyvinylpyrrolidone | 6 |
| Magnesium stearate | 3.0 |

(c)

| Tablet III | mg/tablet |
|---|---|
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

(d)

| Capsule | mg/capsule |
|---|---|
| Compound X | 10 |
| Lactose Ph.Eur. | 389 |
| Croscarmellose sodium | 100 |
| Magnesium stearate | 1.0 |

(e)

| Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)–(c) may be enteric coated by conventional means, for example to provide a coating of cellulose acetate phthalate.

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulphate; evaporation of solvent was carried out using a rotary evaporator under reduced pressure (600–4000 Pascals: 4.5–30 mm Hg) with a bath temperature of up to 60° C.;

(iii) chromatography unless otherwise stated means flash chromatography on silica gel; thin layer chromatography (TLC) was carried out on silica gel plates; where a "Bond Elut™" column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI". Where an "Isolute™ column" is referred to, this means a column containing benzenesulphonic acid (non-endcapped) obtained from International Sorbent Technology Ltd., 1st House, Duffryn Industial Estate. Ystrad Mynach, Hengoed, Mid Glamorgan, UK.

(iv) in general, the course of reactions was followed by TLC and reaction times are given for illustration only;

(v) yields are given for illustration only and are not necessarily those which can be obtained by diligent process development; preparations were repeated if more material was required;

(vi) when given, $^1$H NMR data is quoted and is in the form of delta values for major diagnostic protons, given in parts per million (ppm) relative to tetramethylsilane (TMS) as an internal standard, determined at 300 MHz using per-deuterio DMSO (CD$_3$SOCD$_3$) as the solvent unless otherwise stated: coupling constants (J) are given in Hz;

(vii) chemical symbols have their usual meanings; SI units and symbols are used;

(viii) solvent ratios are given in percentage by volume;

(ix) mass spectra (MS) were run using standard mass spectrometry techniques; where values for m/z are given, generally only ions which indicate the parent mass are reported, and unless otherwise stated the mass ion quoted is the positive mass ion—(M+H)$^-$;

(x) LCMS characterisation was performed using a pair of Gilson 306 pumps with Gilson 233 XL sampler and Waters ZMD4000 mass spectrometer. The LC comprised water symmetry 4.6×50 column C18 with 5 micron particle size. The eluents were: A, water with 0.05% formic acid and B, acetonitrile with 0.05% formic acid. The eluent gradient went from 95% A to 95% B in 6 minutes.

Where indicated ionisation was effected by electrospray (ES); where values for m/z are given, generally only ions which indicate the parent mass are reported, and unless otherwise stated the mass ion quoted is the positive mass ion—(M+H)+; and (xi) the following abbreviations are used:

| | |
|---|---|
| DMSO | dimethyl sulphoxide; |
| DMF | N,N-dimethylformamide; |
| DCM | dichloromethane; |
| EEDQ | 2-ethoxy-1-ethoxycarbonyl-1,2-dihydroquinoline; |
| EtOH | ethanol: |
| EtOAc | ethyl acetate; |
| M.pt. | melting point |
| HATU | O-(7-Azabenzotriazol-1-yl)-N,N,N'N'-tetramethyluronium hexafluorophosphate; and |
| NMP | N-methylpyrrolidinone; |

EXAMPLE 1

1-[1-(3R/S-Phenylbutyl)-piperidin-4-yl]-benzimidazole

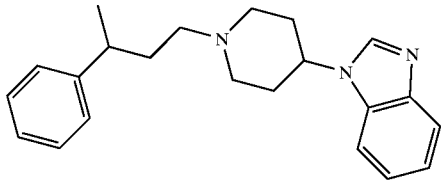

3-(R/S)-Phenylbutyraldehyde (0.25 ml 1.6 mmol) was added to a solution of 1-(1H-piperidin-4-yl)benzimidazole (Method A) (300 mg, 1.5 mmol) in methanol (10 ml) and acetic acid (1 ml) was then added. After 1 hour sodium triacetoxyborohydride (474 mg, 2.2 mmol) was added portionwise over 15 mins and the reaction was left to stir for 70 h. Water (5 ml) was added to the mixture and the methanol was removed in vacuo. The solution was diluted with water (60 ml), and partitioned with EtOAc (3×70 ml). The organic fractions were combined and washed with water (30 ml), dried (MgSO4) and concentrated to give a pale yellow oil. The residue was chromatographed on silica (MPLC) eluting with EtOAc followed by 4% EtOH/EtOAc to give the title compound as a gum (350 mg, 1.05 mmol); NMR: 1.2 (d, 3H), 1.7 (q, 2H), 2.0 (m, 6H), 2.2 (m, 2H), 2.8 (m, 1H), 2.95 (m, 2H), 4.3 (m, 1H), 7.2 (m, 7H), 7.6 (t, 2H) and 8.3 (s, 1H); MS: 334.

EXAMPLE 2

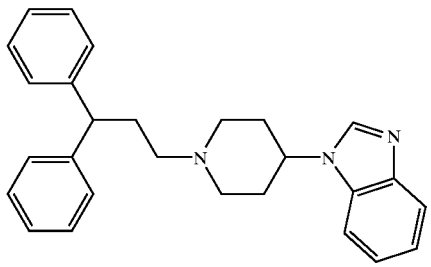

1-[1-(3,3-Diphenylpropyl)-piperidin-4-yl]benzimidazole 3,3-Diphenylpropyl bromide (1.36 g, 5 mmol) was added dropwise to a suspension of potassium carbonate (688 mg, 5 mmol), tetra-butylammonium iodide (10 mg) and 1-(1H-piperidin-4-yl)benzimidazole (Method A) (500 mg, 2.49 mmol) in DMF (15 ml). After 15 h the mixture was poured into 50% brine (30 ml) and extracted with EtOAc (2×50 ml). The combined organics were washed with water (25 ml), dried (MgSO4), concentrated and chromatographed on silica (MPLC) eluting with DCM/EtOAc (1:1) followed by 4% EtOH/EtOAc to give the title compound as a white solid (550 mg, 1.4 mmol); M. pt., 156–157° C.; NMR: 2.0 (m, 6H), 2.25 (m, 4H), 2.95 (m, 2H), 4.0 (t, 1H), 4.3 (m, 1H), 7.2 (2H) and 8.3 (s, 1H); MS: 396.

EXAMPLE 3

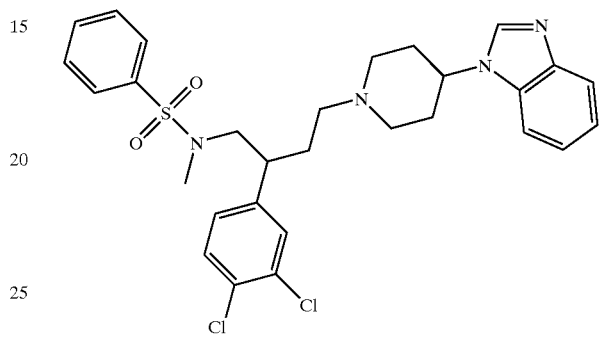

1-[1-(3-{3,4-Dichlorophenyl}-4-{N-methylbenzenesulphonamide}butyl)-piperidin-4-yl]-benzimidazole The procedure shown in Example 2 was followed except that 1-bromo-3-(3,4-dichlorophenyl)-4-(N-methylbenzenesulphonamide)butane (Method G) (114 mg, 0.25 mmol), 1-(1H-piperidin-4-yl)benzimidazole (Method A) (50 mg, 0.23 mmol), potassium carbonate (127 mg, 0.92 mmol) and DMF (7 ml) were used to give the title compound as a solid (20 mg, 0.035 mmol); MS: 571.

EXAMPLE 4

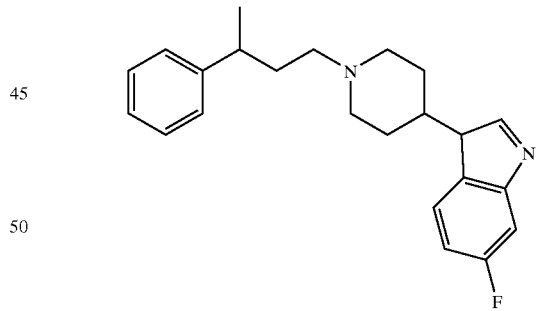

5-Fluoro-1-[1-(3R/S-phenylbutyl)-piperidin-4-yl]benzimidazole

A solution of 2-amino-4-fluoro-1-N-[1-(3R/S-phenylbutyl)-piperidin-4-yl]aniline (prepared as described below) (40 mg, 0.12 mmol), trimethyl orthoformate (0.5 ml, 4.8 mmol) and para-toluenesulphonic acid monohydrate (5 mg, 0.03 mmol) was stirred at 100° C. After 2 h the mixture was cooled and water (2 ml) was added. The solution was partitioned with DCM (2×3 ml) then the organics were combined, dried (MgSO4) and concentrated to give the title compound as an oil that did not need further purification (27 mg, 0.08 mmol); NMR: 1.25 (d, 3H), 1.75 (m, 2H), 2.2 (m, 6H), 2.9 (m, 2H), 4.4 (m, 1H), 7.2 (m, 6H), 7.45 (m, 1H), 7.65 (m, 1H) and 8.4 (s, 1H); MS: 352.

2-Amino-4-fluoro-1-N-[1-(3R/S-phenylbutyl)-piperidin-4-yl]aniline

A mixture of 4-amino-1-(3R/S-phenylbutyl)piperidine (Method E) (500 mg, 1.45 mmol), 2,5-difluoronitrobenzene (0.18 ml, 1.6 mmol) and potassium carbonate (600 mg, 4.4 mmol) in DMSO (5 ml) was heated at 90° C. After 15 h the mixture was poured onto ice and extracted with EtOAc (3×50 ml). The combined organics were dried (MgSO$_4$), concentrated and purified by Bond Elut chromatography (eluting with DCM followed by 50% EtOAc/DCM) to give 4-fluoro-2-nitro-1-N-[1-(3R/S-phenylbutyl)-piperidin-4-yl]aniline as a gum (280 mg, 0.75 mmol); NMR: 1.2 (d, 3H), 1.5 (q, 2H), 1.7 (q, 2H), 1.9 (m, 2H), 2.1 (m, 4H), 2.7 (m, 3H), 3.6 (m, 1H), 7.2 (m, 5H), 7.5 (m, 1H) and 7.8 (m, 2H); MS: 372.

To a stirred solution of suspension of 4-fluoro-2-nitro-1-N-[1-(3R/S-phenylbutyl)-piperidin-4-yl]aniline (275 mg, 0.74 mmol) in methanol (5 ml) was added concentrated HCl (1 ml) followed by stannous chloride dihydrate (300 mg, 1.3 mmol) and the mixture was heated to 100° C. After 2 h, further stannous chloride dihydrate (100 mg), methanol (2 ml) and concentrated HCl (1 ml) were added and the mixture heated to 70° C. After 15 h, further stannous chloride dihydrate (50 mg) and methanol (2 ml) were added and the mixture continued to be heated at 70° C. After 24 h the reaction mixture was concentrated and suspended in water (50 ml) and potassium carbonate was added to neutralise the solution. The solution was extracted with DCM (3×70 ml) and the combined extracts were dried (MgSO$_4$), concentrated and purified by Bond Elut chromatography (eluting with EtOAc followed by 4% EtOH/EtOAc and 1% isopropylamine in 4% EtOH/EtOAc) to give 2-amino-4-fluoro-1-N-[1-(3R/S-phenylbutyl)-piperidin-4-yl]aniline as an oil (210 mg, 0.62 mmol); NMR: 1.2 (d, 3H), 1.35 (q, 2H), 1.7 (m, 2H), 1.9 (m, 4H), 2.1 (m, 2H). 2.7 (m, 3H), 3.0 (m, 3H), 3.9 (d, 1H), 4.8 (br s, 2H), 6.1 (m, 1H), 6.3 (m, 2H) and 7.2 (m, 5H); MS: 342.

EXAMPLE 5–14

The procedure described in Example 4 was repeated using the appropriate starting material (shown below) to replace the 2,5-difluoronitrobenzene to obtain the compounds described in the following table.

| Example No. | Starting Material | Final Product | MS (MH$^+$) |
|---|---|---|---|
| 5 | 2,6-Difluoronitrobenzene | 4-Fluoro-1-[1-(3R/S-phenylbutyl)-piperidin-4-yl]-benzimidazole | 352 |
| 6 | 2,4-Difluoronitrobenzene | 6-Fluoro-1-[1-(3R/S-phenylbutyl)-piperidin-4-yl]-benzimidazole | 352 |
| 7 | 2-Fluoro-4-methyl-nitrobenzene | 6-Methyl-1-[1-(3R/S-phenylbutyl)-pipendin-4-yl]-benzimidazole | 348 |

-continued

| Example No. | Starting Material | Final Product | MS (MH+) |
|---|---|---|---|
| 8 | 2-Fluoro-5-methylnitrobenzene | 5-Methyl-1-[1-(3R/S-phenylbutyl)-piperidin-4-yl]-benzimidazole | 348 |
| 9 | 2,4,5-Trichloronitrobenzene | 5,6-Dichloro-1-[1-(3R/S-phenylbutyl)-piperidin-4-yl]-benzimidazole | 402 |
| 10 | 2,4-Dichloronitrobenzene | 6-Chloro-1-[1-(3R/S-phenylbutyl)-piperidin-4-yl]-benzimidazole | 368 |

-continued

| Example No. | Starting Material | Final Product | MS (MH+) |
|---|---|---|---|
| 11 | 2,3,4-Trichloronitrobenzene | 6,7-Dichloro-1-[1-(3R/S-phenylbutyl)-piperidin-4-yl]-benzimidazole | 402 |
| 12 | 2-Chloro-5-cyanonitrobenzene | 5-Cyano-1-[1-(3R/S-phenylbutyl)-piperidin-4-yl]-benzimidazole | 359 |
| 13 | 2,5-Dichloronitrobenzene | 5-Chloro-1-[1-(3R/S-phenylbutyl)-piperidin-4-yl]-benzimidazole | 368 |
| 14 | 2,6-Dichloro-3-nitropyridine | 6-Chloro-7-aza-1-[1-(3R/S-phenylbutyl)-piperidin-4-yl]-benzimidazole‡ | 369 |

‡This final product was purified on a Bond Elut ™ eluting with DCM, then 5% EtOH/DCM and finally 10% EtOH/DCM.

EXAMPLE 15

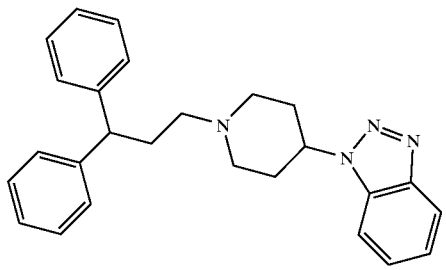

1-[1-(3,3-Diphenylpropyl)-piperidin-4-yl]benzotriazole

The procedure shown in Example 2 was followed except that 3,3-diphenylpropyl bromide (570 mg, 2.1 mmol), 4-benzotriazol-1-yl-piperidine hydrochloride (250 mg, 1.05 mmol), potassium carbonate (580 mg, 4.2 mmol) and DMF (5 ml) were used to give the title compound as a gum (170 mg, 0.43 mmol); NMR: 2.2 (m, 9H), 3.0 (m, 2H), 4.0 (m, 2H), 4.8 (m, 1H), 7.1 (m, 2H), 7.3 (m, 9H), 7.5 (t, 1H), 7.8 (d, 1H) and 8.05 (d, 1H); MS: 397.

EXAMPLE 16

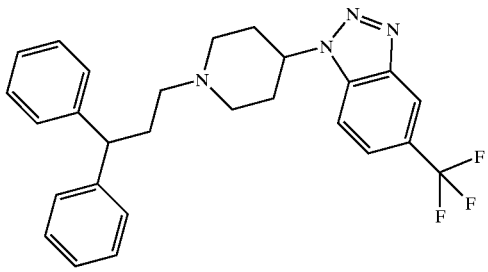

1-[1-(3,3-Diphenylpropyl)-piperidin-4-yl]-5-trifluoromethylbenzotriazole

The procedure shown in Example 2 was followed except that 3,3-diphenylpropyl bromide (570 mg, 2.1 mmol), 4-(5-trifluoromethyl)benzotriazol-1-yl-piperidine hydrochloride (321 mg, 1.05 mmol), potassium carbonate (580 mg, 4.2 mmol) and DMF (5 ml) were used to give the title compound as a gum (320 mg, 0.69 mmol); NMR: 2.2 (m, 9H), 3.0 (d, 2H), 4.0 (m, 2H), 4.9 (m, 1H), 7.1 (m, 2H), 7.3 (m, 8H), 7.8 (d, 1H), 8.15 (d, 1H) and 8.5 (d, 1H); MS: 465.

EXAMPLE 17

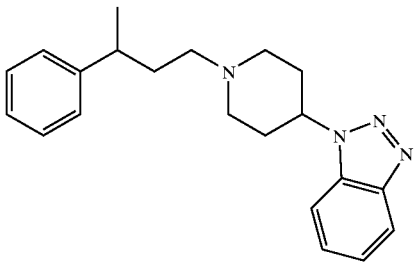

1-[1-(3R/S-Phenylbutyl)-piperidin-4-yl]benzotriazole

The procedure shown in Example 1 was followed except that 3-(R/S)-phenylbutyraldehyde (0.18 ml, 1.2 mmol), 4-benzotriazol-1-yl-piperidine hydrochloride (250 mg, 1.1 mmol), sodium triacetoxyborohydride (334 mg, 1.6 mmol) and acetic acid (0.5 ml) in methanol (5 ml) were used to give the title compound as a white solid (210 mg, 0.63 mmol); NMR: 1.2 (d, 3H), 1.8 (m, 2H), 2.2 (m, 7H), 2.9 (m, 3H), 4.9 (m, 1H), 7.2 (m, 5H), 7.4 (t, 1H), 7.5 (t, 1H), 7.9 (d, 1H) and 8.1 (d, 1H); MS: 335.

EXAMPLE 18

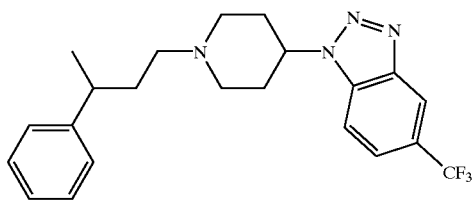

1-[1-(3R/S-Phenylbutyl)-piperidin-4-yl]-5-trifluoromethylbenzotrazole

The procedure shown in Example 1 was followed except that 3-(R/S)-phenylbutyraldehyde (0.18 ml, 1.2 mmol), 4-(5-trifluoromethyl)benzotriazol-1-yl-piperidine hydrochloride (325 mg, 1.1 mmol), sodium triacetoxyborohydride (334 mg, 1.6 mmol) and acetic acid (0.5 ml) in methanol (5 ml) were used to give the title compound as a gum (180 mg, 0.48 mmol); NMR: 1.2 (d, 3H), 1.8 (m, 2H), 2.2 (m, 6H), 2.8 (m, 2H), 3.0 (m, 2H), 4.95 (m, 1H), 7.2 (m, 5H), 7.8 (d, 1H), 8.15 (d, 1H) and 8.5 (s, 1H); MS: 403.

EXAMPLE 19

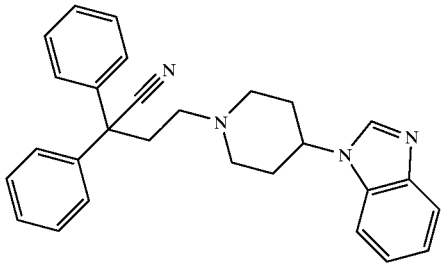

1-[1-(3-Cyano-3,3-diphenylpropyl)-piperidin-4-yl]benzimidazole

4-Bromo-2,2-diphenylbutyronitrile (507 mg, 1.7 mmol) was added dropwise to a suspension of potassium carbonate (234 mg, 1.7 mmol), tetra-butylammonium iodide (10 mg) and 1-(1H-piperidin-4-yl)benzimidazole (Method A) (170 mg, 0.85 mmol) in DMF (10 ml) and the reaction mixture was heated to 90° C. After 15 h the mixture was poured into water (30 ml) and extracted with EtOAc (3×60 ml). The combined organics were dried (MgSO$_4$), concentrated and chromatographed on silica (medium pressure liquid chromatography, MPLC) eluting with DCM followed by 5% EtOH/DCM to give the title compound as a pale yellow solid (70 mg, 0.17 mmol); M. pt., 172–173° C.; NMR: 2.0 (m, 6H), 2.4 (m, 2H), 2.7 (m, 2H), 3.0 (d, 2H), 4.3 (m, 1H), 7.2 (m, 2H), 7.4 (m, 10H), 7.6 (m, 2H) and 8.2 (s, 1H); MS; 422.

EXAMPLE 20

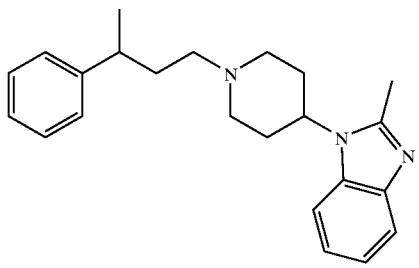

2-Methyl-1-[1-(3R/S-Phenylbutyl)-piperidin-4-yl]-benzimidazole

To a solution of 2-acetamido-1-N-[1-(3R/S-phenylbutyl)-piperidin-4-yl]aniline (Method P) (55 mg, 0.15 mmol) in chloroform (5 ml) was added phosphorous pentachloride (62 mg, 0.3 mmol) and the mixture refluxed. After 3 h the reaction mixture was cooled and water (15 ml) was added carefully followed by potassium carbonate until pH>9. The mixture was then extracted with DCM (2×20 ml) and the combined organics dried (MgSO$_4$), concentrated and chromatographed on silica (MPLC) eluting with DCM followed by 2.5% EtOH/DCM and finally 5% EtOH/DCM to give the title compound as a pale yellow oil (40 mg., 1.15 mmol); NMR: 1.2 (d, 3H), 1.8 (m, 4H), 2.05 (m, 2H), 2.3 (m, 4H), 2.6 (s, 3H), 2.75 (m, 1H), 2.9 (m, 2H), 4.2 (m, 1H), 7.1 (m, 3H), 7.3 (m, 4H) and 7.5 (m, 2H); MS: 342.

EXAMPLE 21

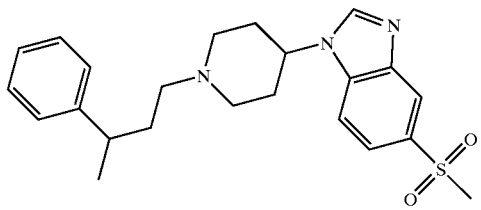

5-Methanesulphonyl-1-[1-(3R/S-phenylbutyl)-piperidin-4-yl]-benzimidazole

A solution of 2-amino-4-methanesulphonyl-1-N-[1-(3R/S-phenylbutyl)-piperidin-4-yl]aniline (prepared as described below) (390 mg, 0.97 mmol), trimethyl orthoformate (3 ml) and para-toluenesulphonic acid monohydrate (15 mg, 0.09 mmol) was stirred at 100° C. After 2 h the mixture was cooled and water (10 ml) was added. The solution was partitioned with DCM (3×30 ml) then the organics were combined, dried (MgSO$_4$) and concentrated to give an oil that was purified first by MPLC eluting with DCM followed by 2.5% EtOH/DCM and then by chromatography (20 g silica Bond Elut™) eluting with DCM followed by 1.5% EtOH/DCM and finally 3% EtOH/DCM to give the title compound as an orange oil (140 mg, 0.34 mmol); NMR: 1.2 (d, 3H), 1.7 (m, 2H), 2.1 (m, 8H), 2.8 (m, 1H), 2.9 (m, 2H), 3.2 (s, 3H), 4.4 (m, 1H), 7.2 (m, 5H), 7.8 (d, 1H), 7.9 (d, 1H), 8.2 (s, 1H) and 8.6 (s, 1H); MS: 412.

2-Amino-4-methanesulphonyl-1-N-[1-(3R/S-phenylbutyl)-piperidin-4-yl]aniline

A mixture of 4-amino-1-(3R/S-phenylbutyl)piperidine di-trifluoroacetate salt (Method E) (1.15 g, 2.5 mmol), 2-fluoro,5-methanesulphonylnitrobenzene (603 mg, 2.75 mmol) and potassium carbonate (1.04 g, 7.5 mmol) in DMSO (10 ml) was heated at 90° C. After 3 h the mixture was poured onto ice and extracted with EtOAc (3×100 ml). The combined organics were dried (MgSO$_4$), concentrated and purified by Bond Elut chromatography (eluting with DCM followed by 25% EtOAc/DCM, 50% EtOAc/DCM, 75% EtOAc/DCM and finally EtOAc) to give 4-methanesulphonyl-2-nitro-1-N-[1-(3R/S-phenylbutyl)-piperidin-4-yl]aniline as a pale yellow oil (790 mg, 1.8 mmol); NMR: 1.2 (d, 3H), 1.6 (m, 4H), 1.9 (m, 2H), 2.1 (m, 4H), 2.7 (m 3H), 3.2 (s, 3H), 3.7 (m, 1H), 7.2 (m, 5H), 7.9 (d, 1H), 8.2 (d, 1H) and 8.5 (m, 1H); MS: 432.

To a stirred solution of suspension of 4-methanesulphonyl-2-nitro-1-N-[1-(3R/S-phenylbutyl)-piperidin-4-yl]aniline (780 mg, 1.81 mmol) in methanol (13 ml) was added concentrated HCl (2.5 ml) followed by stannous chloride dihydrate (1.63 g, 7.2 mmol) and the mixture was heated to 100° C. After 2 h the reaction mixture was concentrated and suspended in water (100 ml) and potassium carbonate was added to basify the solution. The solution was extracted with DCM (3×150 ml) and the combined extracts were dried (MgSO$_4$), concentrated and purified by Bond Elut chromatography (eluting with EtOAc followed by 4% EtOH/EtOAc and 1% isopropylamine in 4% EtOH/EtOAc) to give the title compound as a light brown oil (400 mg, 1 mmol); NMR: 1.2 (m, 3H), 1.4 (m, 2H), 1.7 (m, 2H), 1.9 (m, 4H), 2.1 (m, 2H), 2.8 (m, 3H), 2.95 (s, 3H), 5.0 (m, 3H), 5.75 (s, 1H), 6.95 (m, 2H) and 7.2 (m, 5H); MS: 402.

EXAMPLE 22

Chiral

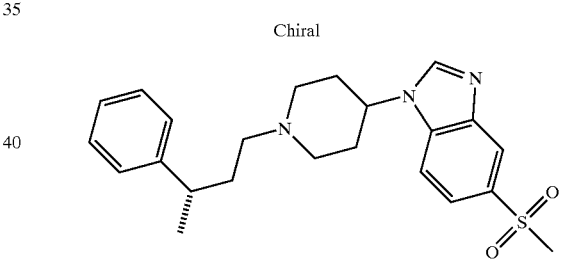

5-Methanesulphonyl-1-[1-(3-S-phenylbutyl)-piperidin-4-yl]-benzimidazole

A solution of 2-amino-4-methanesulphonyl-1-N-[1-(3-S-phenylbutyl)-piperidin-4-yl]aniline (prepared as described below) (440 mg, 1.1 mmol), trimethyl orthoformate (3 ml) and para-toluenesulphonic acid monohydrate (20 mg, 0.11 mmol) was stirred at 100° C. After 15 h the mixture was cooled and water (10 ml) was added. The solution was partitioned with EtOAc (3×40 ml) then the organics were combined, dried (MgSO$_4$) and concentrated to give the title compound as an orange oil (430 mg, 1.05 mmol); NMR: 1.2 (d, 3H), 1.7 (m, 2H), 2.1 (m, 8H), 2.8 (m, 1H), 3.0 (m, 2H), 3.2 (s, 3H), 4.45 (br s, 1H), 7.2 (m, 5H), 7.75 (d, 1H), 7.9 (d, 1H), 8.2 (s, 1H) and 8.6 (s, 1H); MS: 412.

2-Amino-4-methanesulphonyl-1-N-[1-(3-S-phenylbutyl)-piperidin-4-yl]aniline

A mixture of 4-amino-1-N-(3-S-phenylbutyl)piperidine (Method M) (581 mg, 2.5 mmol), 2-fluoro-5-methanesulphonylnitrobenzene (603 mg, 2.75 mmol) and potassium carbonate (1.04 g, 7.5 mmol) in DMSO (10 ml)

was heated at 90° C. After 3 h the mixture was poured onto ice and filtered off; the yellow solid was washed with water and dried to give 4-methanesulphonyl-2-nitro-1-N-[1-(3-S-phenylbutyl)-piperidin-4-yl]aniline as a yellow waxy oil (1.06 g, 2.5 mmol); NMR: 1.2 (d, 3H), 1.6 (m, 4H), 1.9 (m, 2H), 2.1 (m, 4H), 2.7 (m, 3H), 3.2 (s, 3H), 3.7 (m, 1H), 7.2 (m, 5H), 7.9 (m, 1H), 8.2 (m, 1H) and 8.5 (s, 1H); MS: 432.

To a stirred solution of 4-methanesulphonyl-2-nitro-1-N-[1-(3-S-phenylbutyl)-piperidin-4-yl]aniline (1.05 g, 2.44 mmol) in methanol (17 ml) was added concentrated HCl (3 ml) followed by stannous chloride dihydrate (2.2 g, 9.8 mmol) and the mixture was heated to 100° C. After 2 h the reaction mixture was concentrated and suspended in water (100 ml) and potassium carbonate was added to basify the solution. The solution was extracted with DCM (3×150 ml) and the combined extracts were dried (MgSO$_4$), concentrated and purified by Bond Elut chromatography (eluting with EtOAc followed by 4% EtOH/EtOAc and 1% isopropylamine in 4% EtOH/EtOAc) to give the title compound as a light red oil (880 mg, 2.2 mmol); NMR: 1.2 (d, 3H), 1.4 (m, 2H), 1.7 (m, 2H), 1.9 (m, 4H), 2.1 (m, 2), 2.7 (m, 3H), 2.95 (s, 3H), 5.0 (m, 3H), 6.5 (m, 1H), 6.95 (m, 2H) and 7.2 (m, 5H); MS: 402.

EXAMPLE 23

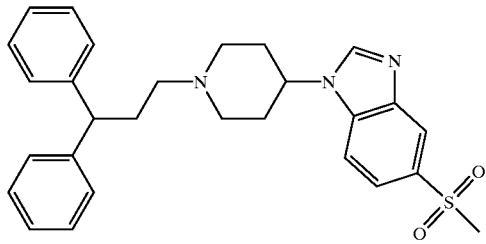

5-Methanesulphonyl-1-[1-(3,3-diphenylpropyl)-piperidin-4-yl]-benzimidazole

A solution of 2-amino-4-methanesulphonyl-1-N-[-1-(3,3-diphenylpropyl)-piperidin-4-yl]aniline (prepared as described below) (50 mg, 0.1 mmol), trimethyl orthoformate (0.7 ml) and para-toluenesulphonic acid monohydrate (2 mg, 0.11 mmol) was stirred at 100° C. After 2.5 h the mixture was cooled and water (10 ml) was added. The solution was partitioned with EtOAc (2×40 ml) then the organics were combined, dried (MgSO$_4$) and concentrated to give the title compound as an oil (47 mg, 0.1 mmol); MS: 474.

2-Amino-4-methanesulphonyl-1-N-[1-(3,3-diphenylpropyl)-piperidin-4-yl]aniline

A mixture of 4-amino-1-N-(3,3-diphenylpropyl)piperidine di-trifluoroacetate (Method I) (500 mg, 0.96 mmol), 2-fluoro-5-methanesulphonylnitrobenzene (380 mg, 1.47 mmol) and potassium carbonate (700 mg, 5.05 mmol) in DMSO (4 ml) was heated at 90° C. After 15 h the mixture was poured onto water and extracted with EtOAc (2×30 ml). The organics were combined, washed with brine, dried (MgSO$_4$), concentrated and purified by Bond Elut™ chromatography to give 4-methanesulphonyl-2-nitro-1-N-[1-(3,3-diphenylpropyl)-piperidin-4-yl]aniline as an oil (200 mg, 0.4 mmol); MS: 494.

To a stirred solution of 4-methanesulphonyl-2-nitro-1-N-[1-(3,3-diphenylpropyl)-piperidin-4-yl]aniline (200 mg, 0.4 mmol) in methanol (4 ml) was added concentrated HCl (1 ml) followed by stannous chloride dihydrate (620 mg) and the mixture was heated to 95° C. After 3 h the reaction mixture was concentrated and suspended in water (100 ml) and potassium carbonate was added to basify the solution. The solution was extracted with EtOAc (150 ml) and the emulsion left to separate. The mixture was then filtered through Celite™, separated, dried (MgSO$_4$), concentrated and purified by Bond Elut™ chromatography (using 1% to 7.5% EtOH in DCM) to give the title compound as an oil (50 mg, 0.11 mmol); MS: 464.

EXAMPLE 24

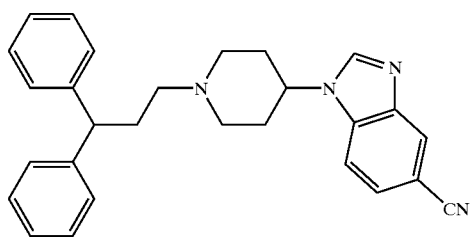

5-Cyano-1-[1-(3,3-diphenylpropyl)-piperidin-4-yl]-benzimidazole

A solution of 2-amino-4-cyano-1-N-[1-(3,3-diphenylpropyl)-piperidin-4-yl]aniline (prepared as described below) (60 mg, 0.15 mmol), trimethyl orthoformate (0.7 ml) and para-toluenesulphonic acid monohydrate (2 mg, 0.11 mmol) was stirred at 100° C. After 2.5 h the mixture was cooled and water (10 ml) was added. The solution was partitioned with EtOAc (2×40 ml) then the organics were combined, dried (MgSO$_4$) and concentrated to give the title compound as an oil (58 mg, 0.15 mmol); MS: 421.

2-Amino-4-cyano-1-N-[1-(3,3-diphenylpropyl)-piperidin-4-yl]aniline

A mixture of 4-amino-1-(3,3-diphenylpropyl)piperidine di-trifluoroacetate (Method I) (500 mg, 0.96 mmol), 2-chloro,3-nitrobenzonitrile (373 mg, 2.04 mmol) and potassium carbonate (700 mg, 5.05 mmol) in DMSO (4 ml) was heated at 90° C. After 15 h the mixture was poured onto water and extracted with EtOAc (2×30 ml). The organics were combined, washed with brine, dried (MgSO$_4$), concentrated and purified by Bond Elut™ chromatography to give 4-cyano-2-nitro-1-N-[1-(3,3-diphenylpropyl)-piperidin-4-yl]aniline as an oil (300 mg, 0.68 mmol), MS: 442.

To a stirred solution of 4-cyano-2-nitro-1-N-[1-(3,3-diphenylpropyl)-piperidin-4-yl]aniline (300 mg, 0.68 mmol) in methanol (4 ml) was added concentrated HCl (1 ml) followed by stannous chloride dihydrate (620 mg) and the mixture was heated to 95° C. After 3 h the reaction mixture was concentrated and suspended in water (100 ml) and potassium carbonate was added to basify the solution. The solution was extracted with EtOAc (150 ml) and the emulsion left to separate. The mixture was then filtered through Celite™, separated. dried (MgSO$_4$), concentrated and purified by Bond Elut™ chromatography (using 1% to 7.5% EtOH in DCM) to give the title compound as an oil (60 mg, 0.15 mmol); MS: 411.

EXAMPLE 25

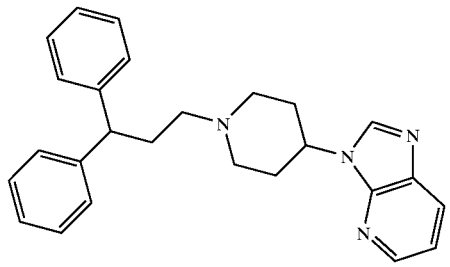

7-Aza-1-[1-(3,3-diphenylpropyl)-piperidin-4-yl]-benzimidazole

A solution of 2-amino-5-aza-1-N-[1-(3,3-diphenylpropyl)-piperidin-4-yl]aniline (prepared as described below) (35 mg, 0.09 mmol), trimethyl orthoformate (0.7 ml) and para-toluenesulphonic acid monohydrate (2 mg, 0.11 mmol) was stirred at 100° C. After 2.5 h the mixture was cooled and water (10 ml) was added. The solution was partitioned with EtOAc (2×40 ml) then the organics were combined, dried (MgSO$_4$) and concentrated to give the title compound as an oil (21 mg 0.05 mmol); MS: 397.

2-Amino-6-aza-1-N-[1-(3,3-diphenylpropyl)-piperidin-4-yl]aniline

A mixture of 4-amino-1-(3,3-diphenylpropyl)piperidine di-trifluoroacetate (Method I) (500 mg, 0.96 mmol), 2-chloro-3-nitropyridine (323 mg, 2.04 mmol) and potassium carbonate (700 mg, 5.05 mmol) in DMSO (4 ml) was heated at 90° C. After 15 h the mixture was poured onto water and extracted with EtOAc (2×30 ml). The organics were combined, washed with brine, dried (MgSO$_4$), concentrated and purified by Bond Elut™ chromatography to give 6-aza-2-nitro-1-N-[1-(3,3-diphenylpropyl)-piperidin-4-yl]aniline the as an oil (350 mg, 0.84 mmol); MS: 417.

To a stirred solution of 6-aza-2-nitro-1-N-[1-(3,3-diphenylpropyl)-piperidin-4-yl]aniline (350 mg, 0.84 mmol) in methanol (4 ml) was added concentrated HCl (1 ml) followed by stannous chloride dihydrate (620 mg,) and the mixture was heated to 95° C. After 3 h the reaction mixture was concentrated and suspended in water (100 ml) and potassium carbonate was added to basify the solution. The solution was extracted with EtOAc (150 ml) and the emulsion left to separate. The mixture was then filtered through Celite™, separated dried (MgSO$_4$), concentrated and purified by Bond Elut™ chromatography (using 1% to 7.5% EtOH in DCM) to give the title compound as an oil (35 mg, 0.09 mmol); MS: 387.

EXAMPLE 26

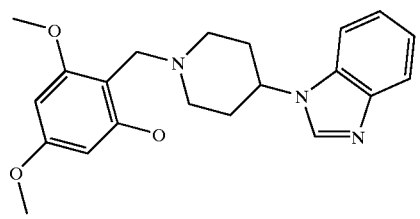

1-[2,4-Dimethoxy-6-hydroxyphenylmethyl)-piperidin-4-yl]benzimidazole

To a solution of 2,4-dimethoxy-6-hydroxybenzaldehyde (1.8 mg, 10 μM) in NMP (100 μL) was added a solution of 1-(1H-4-piperidin-4-yl)benzimidazole (Method A) (1.0 mg, 5 μM) and diisopropylethylamine (1 μL, 5.5 μM) in NMP (100 μL). After 1.5 h a solution of sodium triacetoxyborohydride (2.8 mg, 15 μM) in acetonitrile: NMP, 1:1 (100 μL) was added. After 16 h at room temperature the reaction mixture was concentrated to give the title compound which was identified by LCMS; MS: 368.

EXAMPLES 27–28

The procedure described in Example 26 was repeated using the appropriate starting material (shown below) to replace the 2,4-dimethoxy-6-hydroxybenzaldehyde to obtain the compounds described in the following table.

| Example No. | Starting Material | Final Product | MS (MH$^+$) |
|---|---|---|---|
| 27 | 4-N,N-Dimethylaminocinnamaldehyde | 1-[{3-(4-N,N-Dimethylaminophenyl)prop-2-E-enyl}-piperidin-4-yl]benzimidazole | 361 |
| 28 | 2,4-Dimethyl,1-N-phenylpyrrole-3-carboxaldehyde | 1-[{2,4-Dimethyl,1-N-phenylpyrrol-3-yl)methyl}-piperidin-4-yl]benzimidazole | 385 |

Method A

1-(1H-4-Piperidin-4-yl)benzimidazole

A suspension of 1-[1-(phenylmethyloxycarbonyl)-piperidin-4-yl]benzimidazole (Method B) (3.44 g, 9.7 mmol) and 10% palladium on carbon (250 mg) in EtOH (150 ml) was stirred at room temperature under a hydrogen atmosphere (1 atm). After 70 h the mixture was filtered through Celite™ and concentrated to give a brown oil. The residue was chromatographed on silica with 10% methanol/DCM as eluant to give the title compound as an oil (1.95 g, 9.7 mmol); NMR: 1.9 (m, 4H), 2.7 (m, 2H), 3.1 (m, 2H), 4.4 (m, 1H), 7.2 (m, 2H), 7.6 (m, 2H) and 8.3 (s, 1H); MS: 202.

Method B

1-[1-(Phenylmethyloxycarbonyl)-piperidin-4-yl]benzimidazole

A solution of 2-amino-1-N-[1-(phenylmethyloxycarbonyl)-piperidin-4-yl]aniline (Method C) (500 mg, 1.4 mmol), trimethyl orthoformate (1 ml, 9.7 mmol) and para-toluenesuphonic acid monohydrate (30 mg, 0.16 mmol) were stirred at 100° C. After 2 h the mixture was cooled and water (10 ml) was added. The solution was partitioned with EtOAc (3×20 ml) then the organics were combined, washed with water (10 ml), dried ($MgSO_4$) and concentrated to give the title compound as an oil that did not need further purification (410 mg, 1.2 mmol); NMR: 2.0 (m, 4H), 3.0 (m, 2H), 4.2 (d, 2H), 4.6 (m, 1H), 5.1 (s, 2H), 7.2 (m, 2H), 7.4 (m, 5H), 7.65 (d, 2H) and 8.3 (s, 1H); MS: 336.

Method C

2-Amino-1-N-[1-(phenylmethyloxycarbonyl)-piperidin-4-yl]aniline

To a stirred suspension of Raney nickel (510 mg) in THF (40 ml) was added 2-nitro-1-N-[1-(phenylmethyloxycarbonyl)-piperidin-4-yl]aniline (Method D) (200 mg, 0.56 mmol) and the mixture was stirred under a hydrogen atmosphere (1 atmosphere). After 15 h the mixture was filtered through Celite™, concentrated and purified by column chromatography (eluting with 25% EtOAc/DCM) to give the title compound as an oil (50 mg, 0.15 mmol); NMR: 1.3 (m, 2H), 1.9 (m, 2H), 3.0 (m, 2H), 3,3 (m, 2H),3.9 (m, 1H), 4.1 (d, 1H), 4.45 (br s, 2H), 5.05 (s, 2H), 6.4 (m, 4H) and 7.3 (m, 5H); MS: 326.

Method D

2-Nitro-1-N-[1-(phenylmethyloxycarbonyl)-piperidin-4-yl]aniline

A suspension of 2-fluoronitrobenzene (3.52 g, 25 mmol), 4-amino-1-(phenylmethyloxycarbonyl)piperidine† (4.0 g, 17 mmol) and potassium carbonate (64 g, 19 mmol) in DMSO (25 ml) was heated to 100° C. After 5 h the mixture was poured into ice/water and the resulting yellow solid was collected by filtration and washed with water. The solid was dried to give the title compound as a yellow solid (5.69 g, 16 mmol); NMR: 1.6 (m, 2H), 2.1 (d, 2H), 3.1 (t, 2H), 3.7 (m, 1H), 4.1 (d, 2H), 5.2 (s, 2H), 6.7 (t, 1H), 6.9 (d, 1H), 7.3–7.5 (m, 6H), 8.1 (d, 1H) and 8.2 (dd, 1H); MS: 356.

† Compound described in EP-A-0309422

Method E

4-Amino-1-(3R/S-phenylbutyl)piperidine

To a solution of 4-tert-butoxycarbonylamino-1-(3R/S-phenylbutyl)piperidine (Method F) (13.1 g, 39.5 mmol) in DCM (150 ml) was added trifluoroacetic acid (30 ml) dropwise. After 15 h, toluene was added and the reaction mixture was concentrated to give the di-trifluoroacetic acid salt of the title compound as an oil (12.8 g, 27.8 mmol); MS: 233.

Method F

4-tert-Butoxycarbonylamino-1-(3R/S-phenylbutyl)piperidine

To a stirred solution of 4-(tert-butoxycarbonylamino) piperidine (45 g, 0.225 mol) in methanol (160 ml) was added 3-phenylbutyraldehyde (36.5 ml, 0.25 mol) followed by acetic acid (15 ml). After 1 h, sodium triacetoxyborohydride (71.5 g, 0.34 mol) was added portionwise over 30 mins [Caution: effervescence and exotherm]. After 15 h water (60 ml) was added and the total mixture was concentrated to remove methanol. Water (250 ml) was added and the mixture was extracted with EtOAc (3×500 ml). The combined organics were washed with water, brine and dried ($MgSO_4$) to give the title compound as a white solid that was further recrystallised from DCM/EtOAc (54.1 g, 0.163 mol); M. pt. 220–221° C.; NMR: 1.2 (m, 3H), 1.4 (s, 9H), 1.7 (m, 2H), 2.0 (m, 6H), 2.8 (m, 4H), 3.3 (m, 2H), 7.0 (br s, 1H), 7.3 (m, 5H); MS: 333.

Method G

1-Bromo-3-(3,4-dichlorophenyl)-4-(N-methylbenzenesulphonamide)butane

To a solution of 3-(3,4-dichlorophenyl)-4-(N-methylbenzenesulphonamide)butan-1-ol (prepared as described below) (257 mg, 0.66 mmol) in DCM (20 ml) was added carbon tetrabromide (232 mg, 0.7 mmol) followed by triphenylphosphine (183 mg, 0.7 mmol). After 5 hours the solution was concentrated and then purified by Bond Elut™ chromatography (eluting with dichloromethane) to give the title compound as an oil, which solidified on standing (290 mg, 0.64 mmol); NMR: 2.07 (m, 1H), 2.38 (m, 1H), 2.69 (s, 3H), 3.06 (dd, 1H), 3.10 (dd, 1H), 3.17 (m, 1H), 3.40 (m, 2H), 7.07 (dd, 1H), 7.28 (d, 1H), 7.40 (d, 1H), 7.55 (m, 3H) and 7.77 (d, 2H).

3-(3,4-Dichlorophenyl)-4-(N-methylbenzenesulphonamide)butan-1-ol

Sodium hydride (57.4 g, 60% dispersion in oil, 1.43 mol) was added to a 3 L, 3-necked flask (fitted with mechanical stirrer, exit needle and condenser) and suspended in THF (900 ml). A solution of 3,4-dichlorophenylacetonitrile (257 g, 1.38 mol) in THF (400 ml) was added to the ice-cooled flask via cannula over a period of 1 hour. The mixture was then stirred at room temperature for 1.5 hours during which time there was vigorous gas evolution. The reaction mixture was then ice-cooled and 2-(2-bromoethyl)oxytetrahydropyran (288.5 g, 1.38 mol) was added via teflon cannula under nitrogen pressure over a period of 30 mins. After 40 hours the reaction mixture was quenched with ammonium chloride (10 ml), concentrated (to remove the THF) and water was added. The mixture was extracted with DCM and the organic extracts dried ($Na_2SO_4$), concentrated and distilled under reduced pressure (174° C., 100 mtorr) to give an oil. This residue was purified by flash column chromatography (hexane to 1:1, hexane: DCM) to give 2-(3-cyano-3-[3,4-dichlorophenyl]propyl)oxytetrahydropyran as an oil (210 g, 0.67 mol).

Raney nickel (38 g) was placed in a stainless steel bottle and EtOH (100 ml) was added followed by a solution of 2-(3-cyano-3-(3,4-dichlorophenyl)propyl)oxytetrahydropyran (138 g, 0.44 mol) in EtOH (1100 ml) and concentrated ammonium hydroxide (600 ml). The bottle was then shaken under an atmosphere of hydrogen gas (53 psi) and when the pressure fell below 35 psi the flask was repressurised. After 24 h the pressure remained constant so the reaction mixture was filtered through Celite™ and concentrated. Water was added, the mixture was extracted with DCM and then dried ($Na_2SO_4$) and concentrated to give 2-(3-(3,4-dichlorophenyl)-4-aminobutyl) oxytetrahydropyran as an oil (75 g, 0.24 mol).

To a stirred solution of 2-(3-[3,4-dichlorophenyl]-4-aminobutyl)oxytetrahydropyran (2 g, 6.3 mmol) in DCM (50 ml) was added triethylamine (1.3 ml, 9.4 mmol) followed by benzenesulphonyl chloride (0.82 ml. 6.4 mmol). After 15 hours the reaction mixture was diluted with DCM, washed with hydrochloric acid (0.3M, 50 ml), sodium hydroxide (1M, 20 ml), water (20 ml), dried ($Na_2SO_4$), concentrated and purified by flash column chromatography (eluting with 1:1 hexane, ether) to give 2-(3-[3,4-dichlorophenyl]-4-(N-benzenesulphonamide)butyl) oxytetrahydropyran as an oil (3.02 g, 6.3 mmol); MS: 462.

Sodium hydride (0.5 g, 60% dispersion in oil, 12.5 mmol) was washed with petroleum ether and DMF (5 ml) was added. A solution of 2-(3-[3,4-dichlorophenyl]-4-(N-benzenesulphonamide)butyl)oxytetrahydropyran (2.6 g, 5.7 mmol) in DMF (15 ml) was then added via cannula and the mixture was left to stir until bubbling ceased at which point methyl iodide (0.7 ml, 11.2 mmol) was added in one portion. After 2 hours the reaction was quenched with the dropwise addition of water. Hydrochloric acid (1M, 13 ml) and water (350 ml) were added and the mixture extracted with DCM (3×50 ml). The combined organics were washed with water, dried ($Na_2SO_4$) and concentrated to give 2-(3-[3,4-dichlorophenyl]-4-(N-methylbenzenesulphonamide)butyl) oxytetrahydropyran as an oil (2.6 g, 5.5 mmol).

A solution of 2-(3-[3,4-dichlorophenyl]-4-[N-methylbenzenesulphonamide]butyl)-oxytetrahydropyran (3 g, 6 mmol) in THF (100 ml) and hydrochloric acid (1 M, 50 ml). After 60 h the solution was concentrated to remove THF, then sodium hydroxide (1M solution, 45 ml) was added followed by saturated sodium bicarbonate and the mixture was extracted with ether (3×50 ml). The combined organics were washed with brine, dried ($Na_2SO_4$), concentrated and purified by flash column chromatography (using ether: hexane, 4:1 as eluent) to give 3-(3,4-dichlorophenyl)-4-(N-methylbenzenesulphonamide)butan-1-ol as an oil (1.83 g, 4.7 mmol); MS: 387.

Method H

The ability of compounds to inhibit the binding of RANTES was assessed by an in vitro radioligand binding assay. Membranes were prepared from Chinese hamster ovary cells which expressed the recombinant human CCR5 receptor. These membranes were incubated with 0.1 nM iodinated RANTES, scintillation proximity beads and various concentrations of the compounds of the invention in 96-well plates. The amount of iodinated RANTES bound to the receptor was determined by scintillation counting. Competition curves were obtained for compounds and the concentration of compound which displaced 50% of bound iodinated RANTES was calculated ($IC_{50}$). All of the compounds of Examples 1–28 had an $IC_{50}$ of less than 50 μM.

Method I

4-Amino-1-(3,3-diphenylpropyl)piperidine

To a solution of 4-tert-butoxycarbonylamino-1-N-(3,3-diphenylpropyl)piperidine (Method J) (10 g, 25 mmol) in DCM (100 ml) was added trifluoroacetic acid (20 ml) dropwise. After 3 h, toluene was added and the reaction mixture was concentrated to give the di-trifluoroacetic acid salt of the title compound as an oil (9.7 g, 19 mmol); MS: 295.

Method J 4-tert-Butoxycarbonylamino-1-N-(3,3-diphenylpropyl) piperidine

To a solution of 4-(Boc-amino) piperidine (10 g, 50 mmol) in acetonitrile (200 ml) was added 3,3-diphenylpropyl bromide (15.1 g, 55 mmol), tetra-butylammonium iodide (2 g, 5 mmol) and potassium carbonate (15 g, 100 mmol) and the mixture refluxed. After 5 h the reaction mixture was cooled and poured into water. The solution was partitioned with EtOAc and the organic layer dried ($MgSO_4$), concentrated and purified by column chromatography (toluene: EtOAc, 1:1 with 1% triethylamine) to give the title compound as an oil (15.9 g, 40 mmol); MS: 395.

Method K 4-tert-Butoxycarbonylamino-1-(3-S-phenyl-1-butanoic amide)piperidine

To a solution of 4-Boc-amino piperidine (2.46 g, 12.3 mmol) in DMF (30 mL) was added HATU (4.67 g, 12.3 mmol), 3-S-phenyl-1-butanoic acid (2 g, 12.2 mmol) and diisopropylethylamine (2.12 mL). The reaction mixture was stirred over night then poured into water and extracted into ethyl acetate. Dried over $MgSO_4$ and evaporated to afford the title compound as a white solid, (4.03 g, 11.6 mmol); NMR: 1.20 (6H, m), 1.38 (9H, s), 1.65 (2H, m), 2.60 (2H, m), 3.00 (1H, m), 3.15 (1H, q), 3.40 (1H, m), 3.80 (1H, d, broad), 4.20 (1H, m), 6.80 (1H, m), 7.18 (1H, m), 7.24 (4H, m) MS: 347, 291 (—BOC).

Method L

4-Amino-1-(3-S-phenyl-1-butanoic amide)piperidine hydrochloride

To a solution of acetyl chloride (5 mL) in methanol (20 mL) was added 4-Boc-amino-1-(3-S-phenyl-1-butanoic amide)piperidine (Method K) (1 g, 3 mmol) and stirred for 1 h. The solvents were then evaporated to afford the title compound as a white solid. (850 mg, 3 mmol); NMR: 1.20 (3H, d), 1.35 (2H, m), 1.41 (1H, m), 1.89 (2H, m), 3.0 (5H, m), 3.90 (1H, d), 4.30 (1H, d), 7.10 (1H, m), 7.20 (4H, m); MS: 247.

Method M

4-Amino-1-(3-S-phenylbutyl)piperidine

To a solution of 4-amino-1-(3-S-phenyl-1-butanoic amide)piperidine (Method L) (850 mg, 3 mmol) in THF (20 mL) was added a solution of $LiAlH_4$ in THF (10 mL of 1.0M solution) and the mixture was refluxed for 5 h. After cooling and quenching with aqueous sodium hydroxide the mixture was filtered and partitioned between water and ethyl acetate. The combined organic phase was dried ($MgSO_4$) and evaporated to afford the title compound as a white solid, (610 mg, 2.6 mmol); NMR: 1.20 (4H, m), 1.60 (4H, m), 1.89 (2H, m), 2.10 (2H, m), 2.43 (1H, m), 2.70 (4H, m), 7.10 (3H, m), 7.20 (2H, m); MS: 233.

Method N

2-Amino-1-[1-(3R/S-phenylbutyl)-piperidin-4-yl]aniline

To a stirred solution of 2-nitro-1-N-[1-(3R/S-phenylbutyl)-piperidin-4-yl]aniline (Method O) (765 mg, 2.16 mmol) in ethanol (10 ml) was added 10% Pd on carbon and the mixture was stirred under a hydrogen atmosphere (1 atmosphere). After 5 h the reaction mixture was filtered through Celite™, concentrated and purified by Bond Elut™ chromatography (using DCM, and 2.5% to 10% EtOH in DCM) to give an oil that still contained impurities. The oil was then purified on an amine retention SCX column eluting first with methanol and then with 2% aqueous ammonia in methanol to give the title compound as an oil (580 mg, 1.8 mmol); NMR: 1.2 (d, 3H), 1.4 (m, 2H), 1.7 (m, 2H), 2.0 (m, 6H), 2.8 (m, 3H), 4.05 (m, 1H), 4.4 (m, 2H), 6.4 (m, 4H) and 7.20 (m, 5H); MS: 324.

Method O
2-Nitro-1-[1-(3R/S-phenylbutyl)-piperidin-4-yl]aniline

A mixture of 4-amino-1-(3R/S-phenylbutyl)piperidine di-trifluoroacetate (Method E) (1 g, 2.17 mmol), 2-fluoronitrobenzene (0.37 ml, 3.5 mmol) and potassium carbonate (1.2g, 8.7 mmol) in DMSO (10 ml) was heated at 90° C. After 2 h the mixture was poured onto water and extracted with EtOAc (3×200 ml). The organics were combined, washed with brine, dried (MgSO$_4$) and concentrated to give the title compound as an oil (765mg, 2.17 mmol); NMR: 1.2 (d, 3H), 1.5 (m, 2H), 1.7 (m, 2H), 1.9 (m, 2H), 2.2 (m, 4H), 2.7 (m, 4H), 3.6 (m, 1H), 6.75 (t, 1H), 7.20 (m, 6H) and 7.4 (m, 2H); MS: 354.

Method P
2-Acetamido-1-N-[1-(3R/S-phenylbutyl)-piperidin-4-yl] aniline

A mixture of 2-amino-1-N-[1-(3R/S-phenylbutyl)-piperidin4-yl]aniline (Method N) (80 mg, 0.25 mmol), acetic acid (0.016 ml, 0.28 mmol) and EEDQ (68 mg, 0.28 mmol) in DCM (3 ml) was stirred. After 15 h the mixture was concentrated and purified by column chromatography (DCM followed by 2.5% EtOH/DCM, 5% EtOH/DCM and finally 5% EtOH/DCM with added 2% isopropylamine to give the title compound as an oil (60 mg, 0.16 mmol); NMR: 1.15 (d, 3H), 1.4 (m, 2H), 1.7 (q, 2H), 2.0 (m, 9H), 2.7 (m, 3H), 4.55 (d, 1H), 6.5 (t, 1H), 6.65 (d, 1H), 6.95 (t, 1H), 7.20 (m, 6H) and 9.05 (s, 1H); MS: 366.

Method Q

The ability of compounds to inhibit the binding of MIP-Iα was assessed by an in vitro radioligand binding assay. Membranes were prepared from Chinese hamster ovary cells which expressed the recombinant human CCR5 receptor. These membranes were incubated with 0.1 nM iodinated MIP-1α, scintillation proximity beads and various concentrations of the compounds of the invention in 96-well plates. The amount of iodinated MIP-1α bound to the receptor was determined by scintillation counting. Competition curves were obtained for compounds and the concentration of compound which displaced 50% of bound iodinated MIP-1α was calculated (IC$_{50}$). All of the compounds of Examples 1, 2, 4, 5, 15, 19, 22, 23 and 24 had an IC$_{50}$ of less than 50 µM.

Scheme I

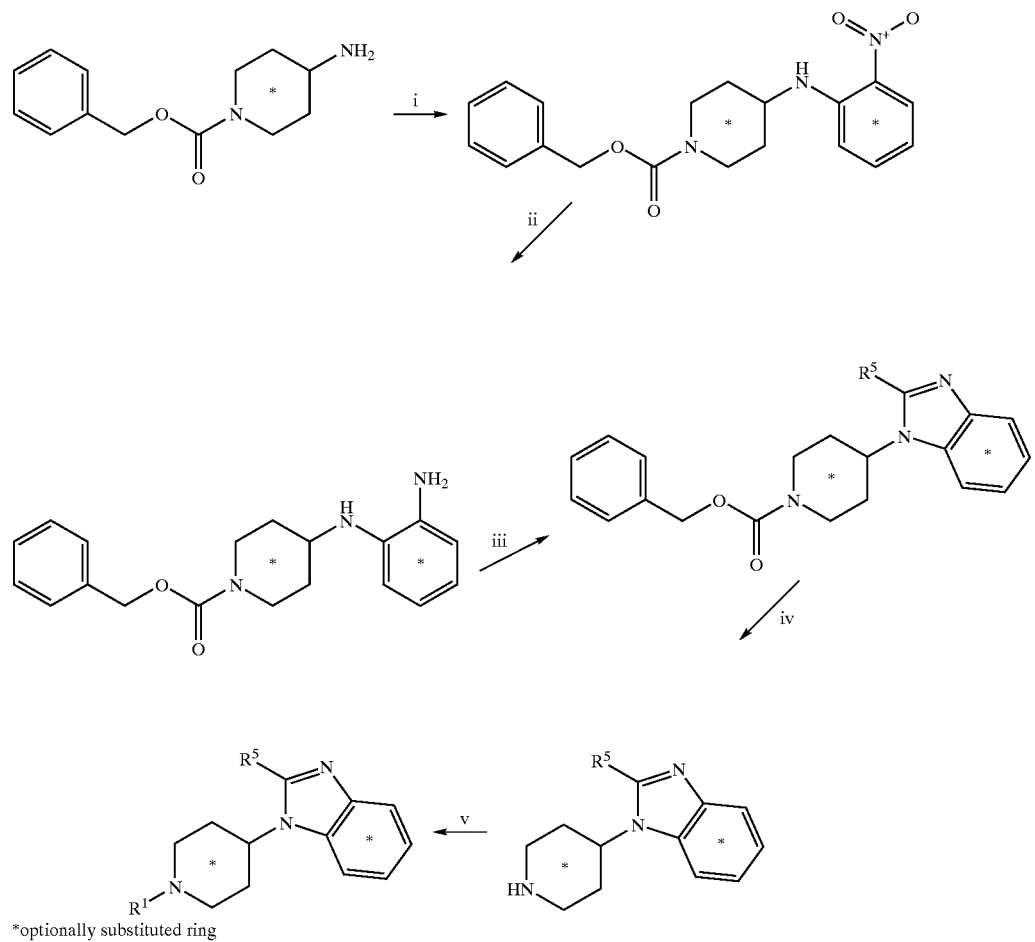

*optionally substituted ring

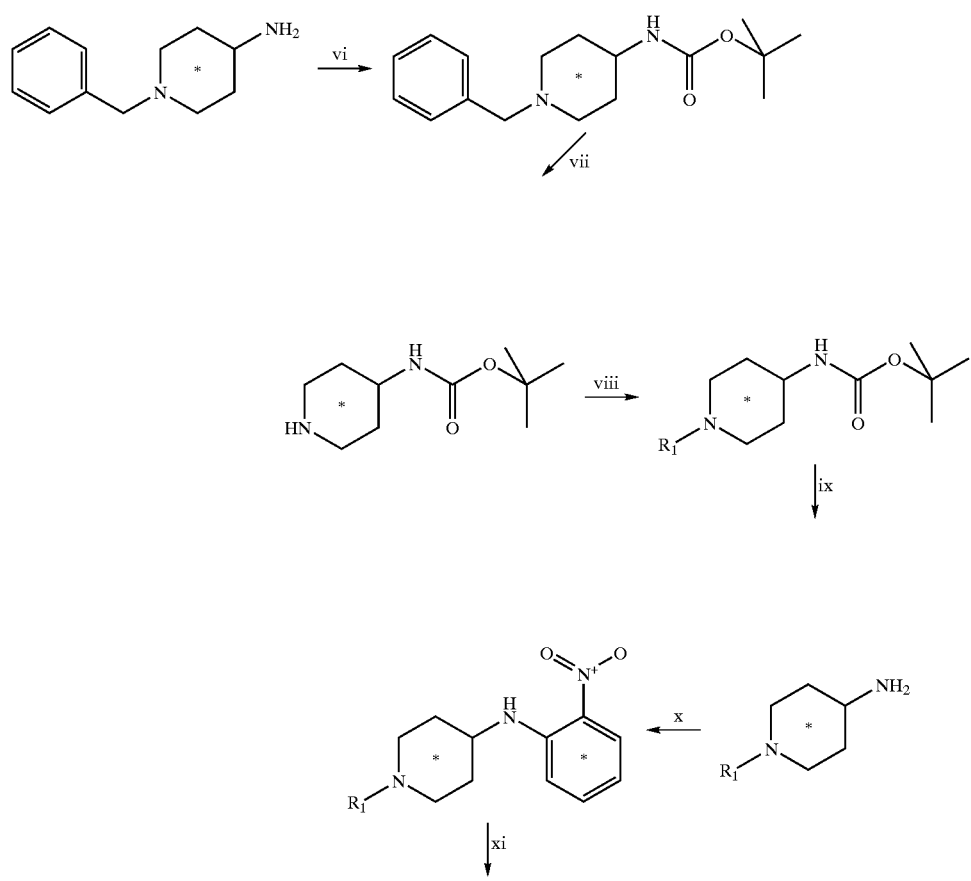
*optionally substituted ring
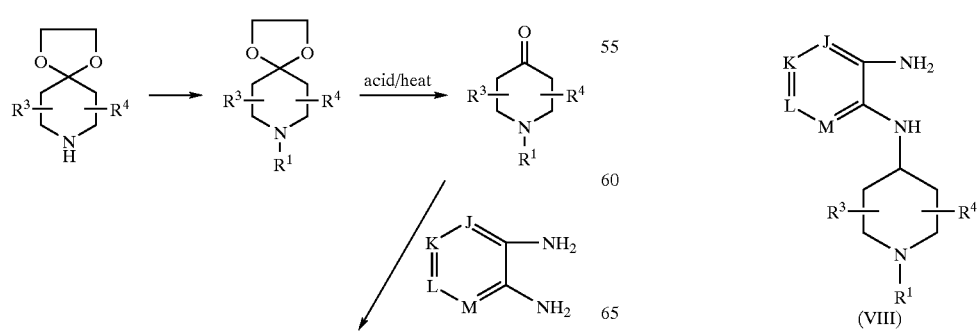

What is claimed is:

1. A compound of formula (Ih):

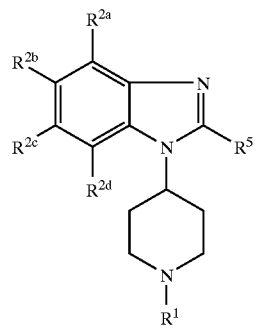
(Ih)

wherein $R^1$ is $CR^{80}R^{81}CR^{82}R^{83}R^{84}$; $R^{84}$ is $CR^{88}R^{89}R^{90}$; $R^{80}$, $R^{81}$, $R^{82}$, $R^{83}$ and $R^{88}$ are, independently, hydrogen or $C_{1-4}$ alkyl; $R^{89}$ is phenyl or heteroaryl; $R^{90}$ is $C_{1-4}$ alkyl, phenyl, or heteroaryl; $R^{2a}$, $R^{2b}$, $R^{2c}$ and $R^{2d}$ are, independently, hydrogen, halogen, cyano, or $S(O)_2(C_{1-4}$ alkyl); and $R^5$ is hydrogen or $C_{1-4}$ alkyl; wherein the foregoing phenyl and heteroaryl groups and moieties are optionally substituted by halogen or $CF_3$;

or pharmaceutically acceptable salt thereof.

2. A compound as claimed in claim 1, wherein $R^{80}$, $R^{81}$, $R^{82}$, $R^{83}$ and $R^{88}$ are all hydrogen.

3. A compound as claimed in claim 1, wherein $R^1$ is $CH_2CH_2CHR^{89}R^{90}$.

4. A compound as claimed in claim 1, wherein $R^{89}$ and $R^{90}$ are both, independently, phenyl.

5. A compound as claimed in claim 1, wherein $R^{89}$ is phenyl substituted by halogen.

6. A process for preparing a compound of formula (Ih) of claim 1, comprising:

i. cyclising a compound of formula (IIa):

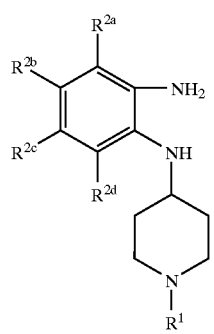
(IIa)

in the presence of $R^5CO_2H$ in refluxing toluene to produce an imidazole ring;

ii. reacting a compound of formula (VIIa):

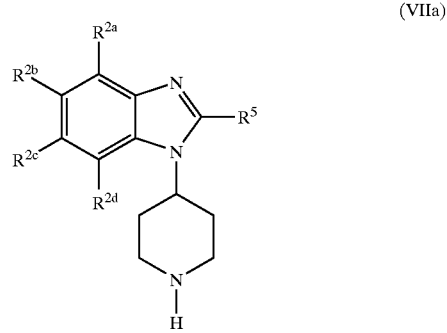
(VIIa)

with a compound of formula $R^1LG$, wherein LG is a leaving group, in the presence of a base; or, iii. reacting a compound of formula (V):

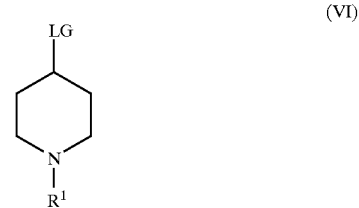
(V)

with a compound of formula (VI)

(VI)
LG
—piperidine—
$R^1$ wherein LG is a leaving group, in the presence of a base.

* * * * *